US011117808B2

(12) United States Patent
Handa et al.

(10) Patent No.: US 11,117,808 B2
(45) Date of Patent: Sep. 14, 2021

(54) MESOPOROUS NITRIC OXIDE-RELEASING SILICA PARTICLES, METHODS OF MAKING, AND USES THEREOF

(71) Applicant: University of Georgia Research Foundation, Inc., Athens, GA (US)

(72) Inventors: Hitesh Handa, Athens, GA (US); Marcus Goudie, Athens, GA (US); Jitendra Pant, Athens, GA (US); Bryan Grommersch, Alpharetta, GA (US); Sean Hopkins, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 85 days.

(21) Appl. No.: 16/051,812

(22) Filed: Aug. 1, 2018

(65) Prior Publication Data

US 2019/0039910 A1    Feb. 7, 2019

Related U.S. Application Data

(60) Provisional application No. 62/539,788, filed on Aug. 1, 2017.

(51) Int. Cl.
*C01B 33/149*    (2006.01)
*A61L 29/08*     (2006.01)
(Continued)

(52) U.S. Cl.
CPC ............ *C01B 33/149* (2013.01); *A61L 27/28* (2013.01); *A61L 27/306* (2013.01);
(Continued)

(58) Field of Classification Search
None
See application file for complete search history.

(56) References Cited

U.S. PATENT DOCUMENTS 6,042,839 A      3/2000  Lahanas et al.
2007/0059350 A1* 3/2007  Kennedy ............ A61L 26/0061
                                                   424/448
(Continued)

OTHER PUBLICATIONS

Frost, M.C. and M.E. Meyerhoff, Synthesis, characterization, and controlled nitric oxide release from S-nitrosothiol-derivatized fumed silica polymer filler particles. Journal of Biomedical Materials Research Part A, 2005. 72(4): p. 409-419.
(Continued)

*Primary Examiner* — Ronak C Patel
(74) *Attorney, Agent, or Firm* — Thomas|Horstemeyer, LLP

(57) ABSTRACT

Nitric oxide-releasing materials, methods of making nitric oxide-releasing materials, and uses of nitric oxide-releasing materials are provided. The nitric oxide-releasing materials include a mesoporous silica core and an outer surface having a plurality of nitric oxide donors. In an exemplary aspects, the nitric oxide-releasing material includes a mesoporous diatomaceous earth core, and an outer surface having a plurality of S-nitroso-N-acetyl-penicillamine groups covalently attached thereto. Uses of the nitric oxide-releasing materials can include coatings for medical devices such as catheters, grafts, and stents; wound gauzes; acne medications; and antiseptic mouthwashes; among others.

10 Claims, 12 Drawing Sheets

(51) Int. Cl.
| | |
|---|---|
| *A61L 29/14* | (2006.01) |
| *A61L 27/28* | (2006.01) |
| *A61L 27/56* | (2006.01) |
| *A61L 31/08* | (2006.01) |
| *A61L 31/14* | (2006.01) |
| *A61L 29/10* | (2006.01) |
| *A61L 27/36* | (2006.01) |
| *A61L 31/16* | (2006.01) |
| *A61L 27/54* | (2006.01) |
| *A61L 27/30* | (2006.01) |
| *A61L 29/16* | (2006.01) |

(52) U.S. Cl.
CPC .......... *A61L 27/3637* (2013.01); *A61L 27/54* (2013.01); *A61L 27/56* (2013.01); *A61L 29/08* (2013.01); *A61L 29/106* (2013.01); *A61L 29/146* (2013.01); *A61L 29/16* (2013.01); *A61L 31/08* (2013.01); *A61L 31/088* (2013.01); *A61L 31/146* (2013.01); *A61L 31/16* (2013.01); *A61L 2300/114* (2013.01); *A61L 2420/04* (2013.01); *C01P 2002/82* (2013.01); *C01P 2004/03* (2013.01); *C01P 2004/61* (2013.01); *C01P 2006/16* (2013.01)

(56) References Cited

U.S. PATENT DOCUMENTS

| | | | |
|---|---|---|---|
| 2009/0162406 | A1 | 6/2009 | Basadonna et al. |
| 2009/0214618 | A1* | 8/2009 | Schoenfisch ............... C07F 7/10 424/426 |
| 2013/0053393 | A1* | 2/2013 | Frangakis ................. A61P 1/04 514/252.16 |
| 2013/0101654 | A1* | 4/2013 | Mathis ................... A01N 55/00 424/405 |
| 2016/0095599 | A1* | 4/2016 | Jose ....................... A61B 17/11 606/154 |

OTHER PUBLICATIONS

Zhang, H., et al., Nitric oxide-releasing fumed silica particles: synthesis, characterization, and biomedical application. Journal of the American Chemical Society, 2003.125(17): p. 5015-5024.

Shin, J.H., S.K. Metzger, and M.H. Schoenfisch, Synthesis of nitric oxide-releasing silica nanoparticles. Journal of the American Chemical Society, 2007. 129(15): p. 4612-4619.

Shin, J.H. and M.H. Schoenfisch, Inorganic/organic hybrid silica nanoparticles as a nitric oxide delivery scaffold. Chemistry of Materials, 2007. 20(1): p. 239-249.

Soto, R.J., L. Yang, and M.H. Schoenfisch, Functionalized mesoporous silica via an aminosilane surfactant ion exchange reaction: controlled scaffold design and nitric oxide release. ACS applied materials & interfaces, 2016. 8(3): p. 2220-2231.

Hetrick, E.M., et al., Anti-biofilm efficacy of nitric oxide-releasing silica nanoparticles. Biomaterials, 2009. 30(14): p. 2782-2789.

Hetrick, E.M., et al., Bactericidal efficacy of nitric oxide-releasing silica nanoparticles. Acs Nano, 2008. 2(2): p. 235-246.

Antonides1, L.E., Diatomite. USGS Mineral Resources Program, 1997.

Calvert, R., Diatomaceous earth. J. Chem. Educ, 1930. 7(12): p. 2829.

Gordon, R., et al., The glass menagerie: diatoms for novel applications in nanotechnology. Trends in biotechnology, 2009 27(2): p. 116-127.

Lopez-Alvarez, M., et al., Silicon-hydroxyapatite bioactive coatings (Si—HA) from diatomaceous earth and silica. Study of adhesion and proliferation of osteoblast-like cells. Journal of Materials Science: Materials in Medicine, 2009. 20(5): p. 1131-1136.

Riccio, D.A., J.L. Nugent, and M.H. Schoenfisch, Stober synthesis of nitric oxide-releasing S-nitrosothiol-modified silica particles Chemistry of Materials, 2011 23(7): p. 1727-1735.

Jaganathan, H. and B. Godin, Biocompatibility assessment of Si-based nano-and micro-particles. Advanced drug delivery reviews, 2012. 64(15): p. 1800-1819.

Anglin, E.J., et al., Porous silicon in drug delivery devices and materials. Advanced drug delivery reviews, 2008. 60 (11): p. 1266-1277.

Grommersch, B.M. et al. Biotemplated Synthesis and Characterization of Mesoporous Nitric Oxide-Releasing Diatomaceous Earth Silica Particles. Applied Materials and Interfaces, 2018, 10, 2291-2301.

* cited by examiner

MESOPOROUS NITRIC OXIDE-RELEASING SILICA PARTICLES, METHODS OF MAKING, AND USES THEREOF

CROSS-REFERENCE TO RELATED APPLICATIONS

This application claims priority to, and the benefit of, U.S. provisional application entitled "MESOPOROUS NITRIC OXIDE-RELEASING SILICA PARTICLES, METHODS OF MAKING, AND USES THEREOF" having Ser. No. 62/539,788, filed Aug. 1, 2017, the contents of which are incorporated by reference in their entirety.

STATEMENT REGARDING FEDERALLY SPONSORED RESEARCH OR DEVELOPMENT

This invention was made with government support under awards K25HL111213 and R01 HL134899 awarded by the National Institutes of Health. The government has certain rights in the invention.

TECHNICAL FIELD

The present disclosure generally relates to nitric oxide donors.

BACKGROUND

Nitric oxide (NO), a gaseous diatomic free radical endogenously produced via the sequential enzymatic oxidation of L-arginine, plays an important and far-reaching role in human physiology [1, 2]. In the 30 years since it was first identified as endothelium-derived relaxing factor, NO has been shown to modulate a number of biological processes such as smooth muscle relaxation, cell proliferation, vasodilation, neurotransmission, cell signaling, the inhibition of platelet adhesion and aggregation, and immune system regulation [1, 3-5]. Nitric Oxide's efficacy in these diverse roles stems from its high membrane diffusivity and excellent reactivity with a variety of chemical species including oxygen, superoxide anions, oxyhemoglobin, thiols, pyrimidine bases, lipids, and metallic complexes [1, 6, 7]. In recent decades, "donor" molecules that release NO at or above physiological levels have been incorporated into a number of biomaterials in order to artificially induce therapeutic effects consistent with those of endogenous NO [4-6, 8-10]. These donor molecules act as NO delivery vehicles, making targeted NO administration feasible by eliminating the spatial and temporal issues surrounding the molecule's short physiological half-life and diffusion distance (1-3 µs and 100-200 µm, respectively) [6, 7, 9, 11, 12].

S-Nitrosothiols (RSNOs) in particular have emerged as one of the most popular classes of NO donors [1, 9, 10]. Synthesized via an acidified nitrosation reaction between thiols (RSH) and nitrite, nitrogen oxides, or alkyl nitrites, RSNOs undergo chemical, photolytic, and thermal decomposition to release NO [9, 13]. S-nitroso-N-acetyl-penicillamine (SNAP), the nitrosated form of N-acetyl-penicillamine (NAP), an amino acid derivative that has been used to treat cystinuria at doses of 2-4 g/day for 155 days with minimal side-effects, is one of the most prevalent RSNO molecules due to its relatively high molecular stability and non-toxic origins [1, 9, 10, 14].

To date, the majority of research in the field of NO technology has focused on the development of antithrombogenic and antimicrobial biomaterials such as catheters, extracorporeal circuitry, biosensors, and biomedical device coatings [12, 15-21]. In addition, NO has also been incorporated into food packaging, acne medications, wound healing materials, and toothpastes [22-25]. The addition of NO donor molecules to these wide-ranging materials is accomplished by either physical (blending or swelling) or chemical means (covalent attachment) [13, 15, 17, 18, 26-29]. Although easier to produce, blended and swollen NO releasing materials often suffer from molecular leaching and diminished release times [12, 13]. The covalent attachment of NO donors to polymer backbones and release scaffolds protects against these limitations, increasing the stability, safety, and application range of materials [12, 13, 30].

A popular material choice for covalently formed NO releasing scaffolds is silicon dioxide due to its chemical inertness, tunable particle size, affordability, and abundance [30-35]. A handful of research groups has previously produced silica-based NO scaffolds using a variety of methodologies [30-35]. For instance, Zhang et al. modified fumed silica with amine-containing silylation reagents to create nonporous diazeniumdiolated silica particles (0.2-0.3 µm) that enhanced thromboresistance when embedded in ECC tubing [31]. In a similar fashion, Frost et al. employed silyation agents to tether RSNOs to nonporous fumed silica particles (7-10 nm) and analyzed their release kinetics under various conditions [30]. Shin et al. synthesized nonporous diazeniumdiolated NO releasing silica particles (20-500 nm) de novo via the co-condensation of two silicon alkoxide precursors [32, 33]. Hetrick et al. later tested these particles for anti-biofilm and bactericidal efficacy [36, 37]. Most recently, Soto et al. created diazeniumdiolated porous silica particles (30-1100 nm) using a modified alkoxysilane co-condensation synthesis [34].

Previously synthesized scaffolds have struggled to strike an ideal balance between NO release kinetics, morphology, particle size, and ease of synthesis. Specifically, diazeniumdiolate based silica scaffolds undergo burst release, eliminating all stored nitric oxide within hours and limiting their utility [31-34]. Additionally, virtually all previously reported NO releasing scaffolds have been nonporous and on the nanoscale [30-35]. Mesoporous, micron scale silica RSNO scaffolds have not yet been created.

There remains a need for improved NO donors that overcome the aforementioned deficiencies.

SUMMARY

Nitric oxide donor materials, methods of making nitrogen oxide donor materials, and various articles incorporating the nitrogen oxide donor materials are provided that overcome one or more of the aforementioned deficiencies. In an exemplary aspect, a nitric oxide-releasing material is provided having a mesoporous diatomaceous earth core, and an outer surface having a plurality of S-nitroso-N-acetyl-penicillamine groups covalently attached thereto. The materials can be useful, for instance, in medical devices such as a urinary catheter, a vascular catheter, a graft, or a stent.

In some aspects, a nitric oxide-releasing material is provided having a mesoporous silica core, and an outer surface having a plurality of moieties having a structure according to the following formula

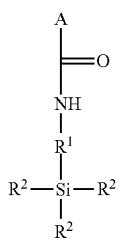

where A is a nitric oxide donor; where $R^1$ is none, a substituted or unsubstituted $C_1$-$C_{20}$ alkyl, a substituted or unsubstituted $C_1$-$C_{20}$ heteroalkyl, a substituted or unsubstituted $C_2$-$C_{20}$ alkenyl, a substituted or unsubstituted $C_2$-$C_{20}$ herteroalkenyl, a substituted or unsubstituted $C_1$-$C_{20}$ alkoxy, or a substituted or unsubstituted $C_1$-$C_{20}$ heteroalkoxy; where each occurrence of $R^2$ is independently a substituted or unsubstituted $C_1$-$C_{20}$ alkyl, a substituted or unsubstituted $C_1$-$C_{20}$ heteroalkyl, a substituted or unsubstituted $C_2$-$C_{20}$ alkenyl, a substituted or unsubstituted $C_2$-$C_{20}$ herteroalkenyl, a substituted or unsubstituted $C_1$-$C_{20}$ alkoxy, a substituted or unsubstituted $C_1$-$C_{20}$ heteroalkoxy, or a bond to an oxygen atom on the outer surface so long as at least one occurrence of $R^2$ is a bond to an oxygen atom on the outer surface.

In some aspects, A is an S-nitrosothiol such as S-nitroso-N-acetyl-penicillamine, S-nitroso-N-acetyl cysteine, S-nitroso-N-acetyl cysteamine, S-nitrosoglutathione, methyl S-nitrosothioglycolate, or a derivative thereof. In some aspects, the nitric oxide donor is a diazeniumdiolate such as diazeniumdiolated dibutylhexanediamine or a derivative thereof.

In some aspects. A has a structure according to the formula $R^4SNO$, where $R^4$ is an amino acid or fragment thereof.

In some aspects, in the formula above, $R^1$ is a substituted or unsubstituted $C_1$-$C_{12}$ alkyl or a substituted or unsubstituted $C_1$-$C_{12}$ aminoalkyl. In some aspects, in the formula above, each occurrence of $R^2$ is independently a substituted or unsubstituted $C_1$-$C_6$ alkyl or a bond to an oxygen atom on the outer surface.

In some aspects, a nitric oxide-releasing material provided herein has a nitric oxide content of about 0.025 μmol to about 0.05 μmol per mg of the nitric oxide-releasing material. In some aspects, a nitric oxide-releasing material provided herein has a half-life for nitric oxide release of about 20 hours to about 40 hours. In some aspects, a nitric oxide-releasing material provided herein an average pore size of about 300 nm to about 600 nm. In some aspects, a nitric oxide-releasing material provided herein is a particle having a longest dimension of about 10 μm to about 20 μm. In some aspects, a nitric oxide-releasing material provided herein includes a mesoporous silica core is selected from the group consisting of a diatomaceous earth, a rice husk, an SAB-3 type mesoporous silica, an HMS type mesoporous silica, MSU-X type mesoporous silica, an SBA-12 type mesoporous silica, an SBA-15 type mesoporous silica, an SBA-16 type mesoporous silica, and an MCM-41 type mesoporous silica.

BRIEF DESCRIPTION OF THE DRAWINGS

Further aspects of the present disclosure will be readily appreciated upon review of the detailed description of its various embodiments, described below, when taken in conjunction with the accompanying drawings.

(FIGS. 7C-7F) scanning electron microscope image of SNAP-DE without (7C, 7E) and with elemental sulfur mapping overlay (7D, 7F), respectively.

DETAILED DESCRIPTION

Figure 1:
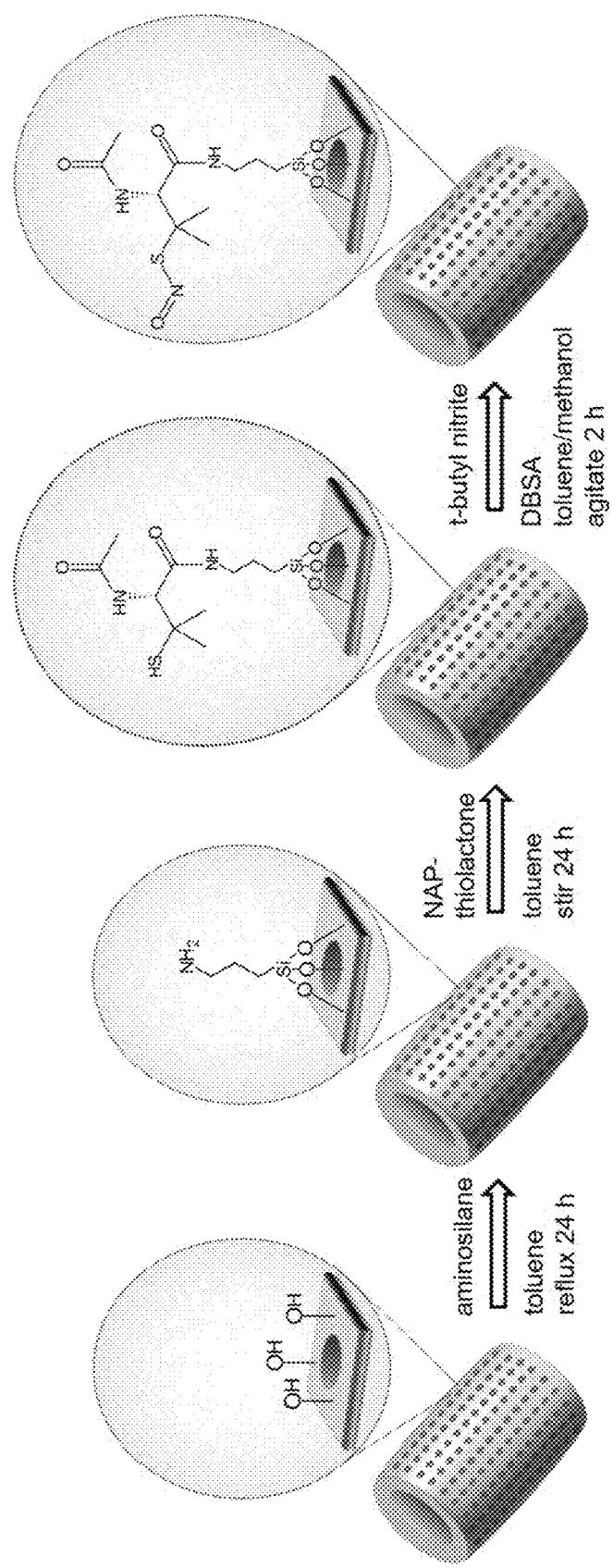
FIG. 1 is a schematic of an exemplary derivatization of nitric oxide-releasing diatomaceous earth using (3-Aminopropyl)triethoxysilane as a representative silane.

In various aspects, nitric oxide-releasing materials are provided. Methods of making and uses of the nitric oxide-releasing materials are also provided.

Diatomaceous earth (DE) consists of the fossilized 10-150 μm shells of diatoms, a class of unicellular marine algae possessing extraordinarily intricate and porous three-dimensional morphologies [35, 38, 39]. With an estimated world reserve of 800 million metric tons and countless applications across the food, cosmetic, chemical, pharmaceutical, and medical industries, diatomaceous earth is a material as ubiquitous as it is versatile [35, 38]. The unique structure of diatoms, coupled with their high amorphous silicon dioxide content (at times 95%), render diatomaceous earth a low density, high surface area, chemically inert, all-natural, abrasive absorptive [35, 38]. Because of these properties, diatomaceous earth is routinely used as a filtration aid, natural detoxifier, cosmetic and personal hygiene abrasive, insecticide, drug delivery and tissue engineering scaffold, wound healing agent, and polymeric filler [35, 38, 40-43]. Chemically modifying diatomaceous earth to release nitric oxide stands to enhance the material's already manifest versatility and efficacy in these biomedical applications and others.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term "reactive coupling group", as used herein, refers to any chemical functional group capable of reacting with a second functional group to form a covalent bond. The selection of reactive coupling groups is within the ability of the skilled artisan. Examples of reactive coupling groups can include primary amines ($-NH_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes ($-COH$) and aldehyde reactive linking groups such as hydrazides, alkoxyamines, and primary amines. Examples of reactive coupling groups can include thiol groups ($-SH$) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The term "protective group", as used herein, refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene, T. W. and Wuts, P. G. M., Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyrl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, I-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, $C_3$-$C_{30}$ for branched chains), 20 or fewer, 12 or fewer, or 7 or fewer. Likewise, in some embodiments cycloalkyls have from 3-10 carbon atoms in their ring structure, e.g. have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, or from one to six carbon atoms in its backbone structure. Likewise, "lower alkenyl" and "lower alkynyl" have similar chain lengths. Throughout the application, preferred alkyl groups are lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In some embodiments, the "alkylthio" moiety is represented by one of —S-alkyl, —S-alkenyl, and —S-alkynyl. Representative alkylthio groups include methylthio, and ethylthio. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, and tert-butoxy. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula:

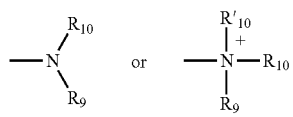

wherein $R_9$, $R_{10}$, and $R'_{10}$ each independently represent a hydrogen, an alkyl, an alkenyl, —$(CH_2)_m$—$R_8$ or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., $R_9$, $R_{10}$ and the nitrogen together do not form an imide. In still other embodiments, the term "amine" does not encompass amides, e.g., wherein one of $R_9$ and $R_{10}$ represents a carbonyl. In additional embodiments, $R_9$ and $R_{10}$ (and optionally $R'_{10}$) each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

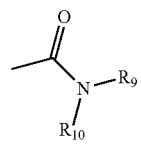

wherein $R_9$ and $R_{10}$ are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, and —CN.

The term "carbonyl" is art-recognized and includes such moieties as can be represented by the general formula:

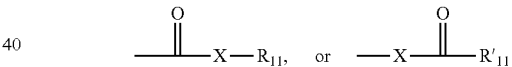

wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "monoester" as used herein refers to an analogue of a dicarboxylic acid wherein one of the carboxylic acids is functionalized as an ester and the other carboxylic acid is a free carboxylic acid or salt of a carboxylic acid.

Examples of monoesters include, but are not limited to, to monoesters of succinic acid, glutaric acid, adipic acid, suberic acid, sebacic acid, azelaic acid, oxalic and maleic acid.

The term "heteroatom" as used herein means an atom of any element other than carbon or hydrogen. Examples of heteroatoms are boron, nitrogen, oxygen, phosphorus, sulfur and selenium. Other heteroatoms include silicon and arsenic.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valences of the heteroatoms.

In various aspects, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, $-CN$, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

The term "copolymer" as used herein, generally refers to a single polymeric material that is comprised of two or more different monomers. The copolymer can be of any form, such as random, block, graft, etc. The copolymers can have any end-group, including capped or acid end groups.

The terms "mean particle size" and "average particle size," as used interchangeably herein, generally refer to the statistical mean particle size (diameter) of the particles in the composition.

The terms "mean pore size" and "average pore size," as used interchangeably herein, generally refer to the statistical mean pore size (diameter) of the pores in a porous material.

The terms "monodisperse" and "homogeneous size distribution", as used interchangeably herein, describe a population of particles or pores all having the same or nearly the same size. As used herein, a monodisperse distribution refers to distributions in which 90% of the particles or pores in the distribution have a size that lies within 5% of the mean size for the distribution.

As used herein, the term "linker" refers to a carbon chain that can contain heteroatoms (e.g., nitrogen, oxygen, sulfur, etc.) and which may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 atoms long. Linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. Those of skill in the art will recognize that each of these groups may in turn be substituted. Examples of linkers include, but are not limited to, pH-sensitive linkers, protease cleavable peptide linkers, nuclease sensitive nucleic acid linkers, lipase sensitive lipid linkers, glycosidase sensitive carbohydrate linkers, hypoxia sensitive linkers, photo-cleavable linkers, heat-labile linkers, enzyme cleavable linkers (e.g., esterase cleavable linker), ultrasound-sensitive linkers, and x-ray cleavable linkers.

Nitric Oxide-Releasing Materials

A variety of nitric oxide-releasing materials are provided. The nitric oxide-releasing materials with mesoporous structures can provide for controllable and sustained release of nitric oxide, even in biological environments. An exemplary nitric oxide-releasing material includes a mesoporous diatomaceous earth core, and an outer surface having a plurality of S-nitroso-N-acetyl-penicillamine groups covalently attached thereto. The diatomaceous earth core provides an inexpensive and readily available bio-derived mesoporous silica core capable of dimensions of about 10 µm to about 20 µm and with highly ordered pores with an average pore size of about 300 nm to about 600 nm.

The nitric-oxide-releasing materials can provide high nitric oxide content (nitric oxide loading). For example, in some aspects the nitric oxide content is about 0.025 µmol to about 0.05 µmol per mg of the nitric oxide-releasing material (µmol/mg). In some aspects, the nitric oxide content is about 0.02-0.08 µmol/mg, about 0.025-0.08 µmol/mg, about 0.03-0.08 µmol/mg, about 0.04-0.08 µmol/mg, or higher.

The nitric oxide-releasing materials can provide for prolonged and sustained release for a period of days. In some aspects, the nitric oxide-releasing material has a half-life for nitric oxide release of about 15 hours, about 20 hours, about 25 hours, about 30 hours, or more. In some aspects, the half-life for nitric oxide release is about 15 hours to 50 hours, about 20 hours to 50 hours, about 20 hours to 40 hours, about 25 hours to 40 hours, or about 25 hours to 50 hours.

The nitric oxide-releasing materials can be used in a variety of applications. For example, in some aspects the nitric oxide-releasing materials are used in medical devices. For example, a surface of the medical device can include a nitric oxide-releasing materials described herein. Medical devices can include any suitable medical device, for example a urinary catheter, a vascular catheter, a graft, or a stent. The nitric oxide-releasing materials can also be used in wound treatment and/or in the prevention of infections, etc. For example, in some aspects a wound gauze is provided that has an absorbent material including a nitric oxide-releasing material described herein. The nitric oxide-releasing materials can also be used in acne medications, e.g. in a facial cream, facial lotion, or a medicated facial wash. In some aspects, antiseptic mouthwashes are provided containing the nitric oxide-releasing materials.

In some aspects, a nitric oxide-releasing material is provided having a mesoporous diatomaceous earth core, and an outer surface having a plurality of S-nitroso-N-acetyl-penicillamine groups covalently attached thereto. In some aspects, a nitric oxide-releasing material is provided having a mesoporous silica core, and an outer surface having a plurality of S-nitrosothiols covalently attached thereto. In some aspects, a nitric oxide-releasing material is provided having a mesoporous silica core having an outer surface, a plurality of nitric oxide donors, and a plurality of amide linker groups covalently attaching the plurality of nitric oxide donors to the outer surface. In some aspects, a nitric oxide-releasing material is provided having a mesoporous silica core, and an outer surface containing a plurality of moieties having a structure according to the following formula

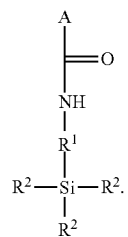

In the above formula, A is a nitric oxide donor. A variety of nitric oxide donors are described below. In some aspects, A is a nitric oxide donor described below. In some aspects, A is S-nitroso-N-acetyl-penicillamine or a derivative or fragment thereof.

In the above formula, $R^1$ can be none. $R^1$ can be a $C_1$-$C_{30}$ alkyl, $C_1$-$C_{20}$ alkyl, $C_2$-$C_{20}$ alkyl, $C_3$-$C_{20}$ alkyl, $C_3$-$C_{15}$ alkyl, $C_3$-$C_{12}$ alkyl, or $C_6$-$C_{12}$ alkyl. The alkyl can be substituted or unsubstituted. $R^1$ can be a $C_1$-$C_{30}$ heteroalkyl, $C_1$-$C_{20}$ heteroalkyl, $C_2$-$C_{20}$ heteroalkyl, $C_3$-$C_{20}$ heteroalkyl, $C_3$-$C_{15}$ heteroalkyl, $C_3$-$C_{12}$ heteroalkyl, or $C_6$-$C_{12}$ heteroalkyl. The heteroalkyl can be substituted or unsubstituted. $R^1$ can be a $C_2$-$C_{30}$ alkenyl, $C_2$-$C_{20}$ alkenyl, $C_3$-$C_{20}$ alkenyl, $C_4$-$C_{20}$ alkenyl, $C_4$-$C_{15}$ alkenyl, $C_4$-$C_{12}$ alkenyl, or $C_6$-$C_{12}$ alkenyl. The alkenyl can be substituted or unsubstituted. $R^1$ can be a $C_1$-$C_{30}$ alkoxy, $C_1$-$C_{20}$ alkoxy, $C_2$-$C_{20}$ alkoxy, $C_3$-$C_{20}$ alkoxy, $C_3$-$C_{15}$ alkoxy, $C_3$-$C_{12}$ alkoxy, or $C_6$-$C_{12}$ alkoxy. The alkoxy can be substituted or unsubstituted. $R^1$ can be a $C_1$-$C_{30}$ heteroalkoxy, $C_1$-$C_{20}$ heteroalkoxy, $C_2$-$C_{20}$ heteroalkoxy, $C_3$-$C_{20}$ heteroalkoxy, $C_3$-$C_{15}$ heteroalkoxy, $C_3$-$C_{12}$ heteroalkoxy, or $C_6$-$C_{12}$ heteroalkoxy. The heteroalkoxy can be substituted or unsubstituted. In some aspects, R1 is a substituted or unsubstituted $C_1$-$C_{12}$ alkyl or a substituted or unsubstituted $C_1$-$C_{12}$ aminoalkyl. Suitable substituents can include any suitable substituent. In some aspects, the substituents include $C_1$-$C_3$ alkyl, $C_1$-$C_3$ heteroalkyl, $C_1$-$C_3$ alkoxy, and $C_1$-$C_3$ heteroalkoxy.

In the above formula, each occurrence of $R^2$ can be selected independent of the other $R^2$ groups so long as at least one occurrence of $R^2$ is a bond to an oxygen atom on the outer surface. In some aspects, exactly 1 occurrence of $R^2$ is a bond to an oxygen atom on the outer surface. In some aspects, exactly 2 occurrences of $R^2$ are a bond to an oxygen atom on the outer surface. In some aspects, every occurrence of $R^2$ is a bond to an oxygen atom on the outer surface. Each occurrence of $R^2$ can be a $C_1$-$C_{30}$ alkyl, $C_1$-$C_{20}$ alkyl, $C_2$-$C_{20}$ alkyl, $C_3$-$C_{20}$ alkyl, $C_3$-$C_{15}$ alkyl, $C_3$-$C_{12}$ alkyl, or $C_6$-$C_{12}$ alkyl. The alkyl can be substituted or unsubstituted. Each occurrence of $R^2$ can be a $C_1$-$C_{30}$ heteroalkyl, $C_1$-$C_{20}$ heteroalkyl, $C_2$-$C_{20}$ heteroalkyl, $C_3$-$C_{20}$ heteroalkyl, $C_3$-$C_{15}$ heteroalkyl, $C_3$-$C_{12}$ heteroalkyl, or $C_6$-$C_{12}$ heteroalkyl. The heteroalkyl can be substituted or unsubstituted. Each occurrence of $R^2$ can be a $C_2$-$C_{30}$ alkenyl, $C_2$-$C_{20}$ alkenyl, $C_3$-$C_{20}$ alkenyl, $C_4$-$C_{20}$ alkenyl, $C_4$-$C_{15}$ alkenyl, $C_4$-$C_{12}$ alkenyl, or $C_6$-$C_{12}$ alkenyl. The alkenyl can be substituted or unsubstituted Each occurrence of $R^2$ can be a $C_1$-$C_{30}$ alkoxy, $C_1$-$C_{20}$ alkoxy, $C_2$-$C_{20}$ alkoxy, $C_3$-$C_{20}$ alkoxy, $C_3$-$C_{15}$ alkoxy, $C_3$-$C_{12}$ alkoxy, or $C_6$-$C_{12}$ alkoxy. The alkoxy can be substituted or unsubstituted. Each occurrence of $R^2$ can be a $C_1$-$C_{30}$ heteroalkoxy, $C_1$-$C_{20}$ heteroalkoxy, $C_2$-$C_{20}$ heteroalkoxy, $C_3$-$C_{20}$ heteroalkoxy, $C_3$-$C_{15}$ heteroalkoxy, $C_3$-$C_{12}$ heteroalkoxy, or $C_6$-$C_{12}$ heteroalkoxy. The heteroalkoxy can be substituted or unsubstituted. In some aspects, each occurrence of $R^2$ is independently a substituted or unsubstituted $C_1$-$C_6$ alkyl or a bond to an oxygen atom on the outer surface. Suitable substituents can include any suitable substituent. In some aspects, the substituents include $C_1$-$C_2$ alkyl, $C_1$-$C_2$ heteroalkyl, $C_1$-$C_2$ alkoxy, and $C_1$-$C_2$ heteroalkoxy.

Mesoporous Silica Cores

The nitric oxide-releasing materials can include a mesoporous silica core. The use of a mesoporous silica core can provide for, among other things, larger and more ordered nitric oxide-releasing materials capable of controlled and sustained nitric oxide release.

In some aspects, the functionalization of the mesoporous silica core results in no or only a negligible change in the size and/or porosity of the mesoporous core. For example, in some aspects, the mesoporous core and the nitric oxide-releasing material have an average pore size of about 200 nm to 2000 nm, about 300 nm to 2000 nm, about 300 nm to 1500 nm, about 300 nm to 1200 nm, about 400 nm to 1200 nm, about 400 nm to 1000 nm, about 400 nm to 800 nm, about 400 nm to 600 nm, or about 300 nm to 600 nm. In some aspects, the mesoporous core and the nitric oxide-releasing material have a longest dimension of about 5 μm to 50 μm, about 10 μm to 50 μm, about 10 μm to 40 μm, about 15 μm to 40 μm, about 15 μm to 30 μm, about 15 μm to 20 μm, or about 10 μm to 20 μm.

In some aspects, the mesoporous silica core is a diatomaceous earth, a rice husk, an SAB-3 type mesoporous silica, an HMS type mesoporous silica, MSU-X type mesoporous silica, an SBA-12 type mesoporous silica, an SBA-15 type mesoporous silica, an SBA-16 type mesoporous silica, or an MCM-41 type mesoporous silica.

In some aspects, the mesoporous silica core is a synthetically derived mesoporous silica. A synthetically derived mesoporous silica core can be prepared, for example, via (1) performing a hydrothermal synthesis reaction with a mixture containing tetraalkoxysilane, a predetermined structure-directing agent, and water to obtain a crystal (silica having a mesoporous structure) and (2) calcining the crystal to obtain mesoporous silica. The structure-directing agent is suitably selected to generate the desired mesoporous silica having the desired structure and pore size. For preparing SAB-3 type mesoporous silica a gemini surfactant (e.g., $C_nH_{2n+1}(CH_3)_2N^+(CH_2)_sN^+(CH_3)_2C_mH_{2m+1}$, wherein n s, and m each represent an integer of 1 or more) can be selected as a structure-directing agent as described in Catalysis Communications, Holland, 2008, Vol. 9, No. 13, p. 2287-2290. For HMS type mesoporous silica, long chain alkylamine ($C_nH_{2n+1}NH_2$, wherein n represents a integer of 1 or more) can be selected as a structure-directing agent as described in Applied Catalysis A: General, Holland, 2008, Vol. 347, p. 133-141. For MSU-X type mesoporous silica, oleyl decaoxyethylene can be selected as a structure-directing agent as described in Microporous and Mesoporous Materials, Holland, 2008, Vol. 109, p. 199-209. For SBA-12 type mesoporous silica, polyethylene oxide can selected as a structure-directing agent as described in Journal of Physical Chemistry B, USA, 2002, Vol. 106, p. 3118-3123. For SBA-15 type mesoporous silica, a triblock copolymer (polyethylene oxide-polypropylene oxide-polyethylene oxide copolymer) can be selected as a structure-directing agent as described in Science, USA, Vol. 279, p. 548-552, and Microporous and Mesoporous Materials, Holland, 2006, Vol. 91, p. 156. For preparing SBA-16 type mesoporous silica, a triblock copolymer (polyethylene oxide-polypropylene oxide-polyethylene oxide copolymer) can be selected as a structure-directing agent as described in Microporous and Mesoporous Materials, Holland, 2007, Vol. 105, p. 15-23. Calcination temperatures and times can be selected by one of skill in the art, but in some aspects will be about 500 to 600° C., and for about 1 to 20 hours.

In some aspects, the mesoporous silica core is a biomimetic mesoporous silica. The use of biomimetic mesoporous silica can provide for complex architectures from the nanoscale to the macroscale without the (often energy inefficient and quite stringent) synthetic conditions required for synthetically derived mesoporous silica. A biomimetic mesoporous silica can include a biosilicate described in Current Opinions in Solid State and Materials Science, Zaremba, 1996, Vol. 1, p. 425-429 and the references cited therein. In some aspects, the mesoporous silica core is derived from plant species such as rice or equisetum or possible diatomaceous origin. This includes, for example diatomaceous earth, diatoms and silicified plant material.

Nitric Oxide Donors

The nitric oxide-releasing material will include a nitric oxide donor. The nitric oxide donor can be an S-nitrosothiol. The S-nitrosothiol can include, for example, S-nitroso-N-acetyl-penicillamine, S-nitroso-N-acetyl cysteine, S-nitroso-N-acetyl cysteamine, S-nitrosoglutathione, methyl S-nitrosothioglycolate, or a fragment or a derivative thereof. The nitric oxide donor can be a diazeniumdiolate, for example diazeniumdiolated dibutylhexanediamine or a fragment or a derivative thereof.

Linkers

The nitric oxide donor will be covalently attached to the surface. In some aspects, the nitric oxide donor can be directly bonded to the surface oxygen. However, in some aspects, the nitric oxide donor is covalently attached to the surface through a linker. A variety of suitable linkers can be included. In some aspects, the linker is a $C_1$-$C_{30}$ alkyl, $C_1$-$C_{20}$ alkyl, $C_2$-$C_{20}$ alkyl, $C_3$-$C_{20}$ alkyl, $C_3$-$C_{15}$ alkyl, $C_3$-$C_{12}$ alkyl, or $C_6$-$C_{12}$ alkyl. The alkyl can be substituted or unsubstituted. In some aspects, the linker is a $C_1$-$C_{30}$ heteroalkyl, $C_1$-$C_{20}$ heteroalkyl, $C_2$-$C_{20}$ heteroalkyl, $C_3$-$C_{20}$ heteroalkyl, $C_3$-$C_{15}$ heteroalkyl, $C_3$-$C_{12}$ heteroalkyl, or $C_6$-$C_{12}$ heteroalkyl. The heteroalkyl can be substituted or unsubstituted. In some aspects, the heteroalkyl is an aminoalkyl. In some aspects, the linker is a $C_1$-$C_{30}$ alkoxy, $C_1$-$C_{20}$ alkoxy, $C_2$-$C_{20}$ alkoxy, $C_3$-$C_{20}$ alkoxy, $C_3$-$C_{15}$ alkoxy, $C_3$-$C_{12}$ alkoxy, or $C_6$-$C_{12}$ alkoxy. The alkoxy can be substituted or unsubstituted. In some aspects, the linker is a a $C_1$-$C_{30}$ heteroalkoxy, $C_1$-$C_{20}$ heteroalkoxy, $C_2$-$C_{20}$ heteroalkoxy, $C_3$-$C_{20}$ heteroalkoxy, $C_3$-$C_{15}$ heteroalkoxy, $C_3$-$C_{12}$ heteroalkoxy, or $C_6$-$C_{12}$ heteroalkoxy. The heteroalkoxy can be substituted or unsubstituted. In some aspects, the linker is a substituted or unsubstituted $C_1$-$C_{12}$ alkyl or a substituted or unsubstituted $C_1$-$C_{12}$ aminoalkyl. Suitable substituents can include any suitable substituent. In some aspects, the substituents include $C_1$-$C_{12}$ primary amines and $C_1$-$C_{12}$ secondary amines.

Methods of Making Nitric Oxide-Releasing Materials

Methods of making nitric oxide-releasing materials are also provided. In some aspects, those of skill in the art will recognize other methods based upon the teachings herein. Such methods are not intended to be excluded, but are rather intended to be included in some aspects of the methods described herein.

In some aspects, the methods of making a nitric oxide-releasing material include (1) silylation of a surface of a mesoporous silica core with a silane having a first reactive coupling group to produce a first functionalized surface; (2) coupling of a thiol having a second reactive coupling group to form a covalent bond with the first reactive coupling group to produce a thiol-functionalized surface; and (3) nitrosylation of a thiol in the thiol-functionalized surface to produce the nitric oxide-releasing material. The first reactive functional group and the second reactive functional group can be any reactive functional group pair described herein, so long as the first reactive functional group and the second reactive functional group are capable of reacting to form a covalent attachment. In some aspects, the first reactive coupling group and the second reactive coupling group are selected from a primary amine and an amine-reactive linking group such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. In some aspects, the first reactive coupling group and the second reactive coupling group are selected from an aldehyde and an aldehyde reactive linking group such as hydrazides, alkoxyamines, and primary amines.

In some aspects, a method of making a nitric oxide-releasing material is provided, the method including (1) silylation of a surface of a mesoporous silica core with an aminosilane to produce an amine-functionalized surface; covalent attachment of a thiolactone to an amine in the amine-functionalized surface to produce a thiol-functionalized surface; and nitrosylation of a thiol in the thiol-functionalized surface to produce the nitric oxide-releasing material. In some aspects, the aminosilane has a structure according to the following formula

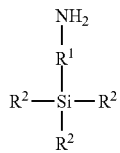

where $R^1$ and $R^2$ are as described above. In some aspects, at least one occurrence of $R^2$ is a methoxy or ethoxy. In some aspects, $R^1$ is a substituted or unsubstituted $C_1$-$C_{12}$ alkyl or a substituted or unsubstituted $C_1$-$C_{12}$ aminoalkyl.

In some aspects, the thiolactone has a structure according to the following formula

where $R^4$ is a substituted or unsubstituted $C_1$-$C_{20}$ alkyl, $C_1$-$C_{12}$ alkyl, $C_2$-$C_{12}$ alkyl, $C_3$-$C_{12}$ alkyl, $C_3$-$C_{15}$ alkyl, $C_3$-$C_{20}$ alkyl, or $C_6$-$C_{12}$ alkyl. The alkyl can be substituted or unsubstituted. In some aspects, the thiolactone has a structure according to the following formula

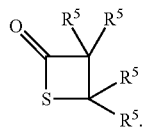

In the above formula, each occurrence of $R^5$ can be independently a hydrogen, a hydroxyl, a substituted or unsubstituted $C_1$-$C_6$ alkyl, substituted or unsubstituted $C_1$-$C_6$ heteroalkyl, a substituted or unsubstituted $C_2$-$C_6$ alkenyl, a substituted or unsubstituted $C_2$-$C_6$ herteroalkenyl, a substituted or unsubstituted $C_1$-$C_6$ alkoxy, or a substituted or unsubstituted $C_1$-$C_6$ heteroalkoxy.

In some aspects, the thiolactone is N-acetyl-D-penicillamine or a fragment or a derivative thereof. In some aspects, the thiolactone is N-Acetylcysteine thiolactone, N-Acetyl-homocysteine thiolactone, Homocysteine thiolactone, Butyryl-homocysteine thiolactone, or a derivative or fragment thereof.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Diatomaceous earth (DE), a nanoporous silica material made of fossilized unicellular marine algae, possesses unique mechanical, molecular transport, optical, and photonic properties exploited across an array of biomedical applications. The utility of DE in many of these applications stands to be enhanced through the incorporation of nitric oxide (NO) technology shown to modulate a number of essential physiological processes. In this work, the preparation and characterization of a bio-templated diatomaceous earth-based nitric oxide delivery scaffold is described for the very first time. Three aminosilanes ((3-Aminopropyl)triethoxysilane (APTES), N-(6-Aminohexyl)aminomethyltriethoxysilane (AHAMTES), and 3-Aminopropyldimethylethoxysilane (APDMES)) were evaluated for their ability to maximize NO loading via the covalent attachment of N-acetyl-D-penicillamine (NAP) to diatomaceous earth. The use of APTES crosslinker resulted in maximal NAP tethering to the DE surface and NAP-DE was converted to NO-releasing S-nitroso-N-acetyl-penicillamine (SNAP)-DE by nitrosation. The total NO loading of SNAP-DE as determined by chemiluminescence was found to be 37.2±7.91 nmol NO/mg. Retention of diatomaceous earth's unique mesoporous morphology throughout the derivatization was confirmed by scanning electron microscopy. SNAP-DE showed 92.95±2.6% killing efficiency against gram positive bacteria S. aureus as compared to the control. The WST-8 based cytotoxicity testing showed no negative impact on mouse fibroblast cells demonstrating its potential biocompatibility. The development of NO releasing diatomaceous earth, presents a unique means of delivering tunable levels of NO to materials across the fields of polymer chemistry, tissue engineering, drug delivery, and wound healing.

In some aspects, the nitric-oxide releasing materials are incorporated into a hydrogel, e.g. a hydrogel strip that can be applied to a target area to deliver nitric-oxide releasing material at the surface. In some aspects, a nitric-oxide releasing material is incorporated into hydrogel strips for dental applications, e.g. for application to dental biofilms. Various bioabsorbable polymers, natural polymers, and hydrogels can be used for the hydrogel component. Pluronic hydrogels are a class of water soluble copolymers made of ethylene oxide (PEO) and polypropylene oxide (PPO) that have been used for a variety of biomedical applications including drug delivery, tissue engineering, and wound therapies. Pluronic hydrogels with various hydrophilicity and molecular weights can be used (e.g., F68, P123, F127)

and dissolved in methanol (100 mg/mL). The hydrogel can be loaded with nitric-oxide releasing materials described herein, e.g. about 1-20% loading or about 5-15% loading by weight.

Example 1

Introduction

In this work, three primary aminosilanes (APTES, AHAMTES, APDMES) were used to tether NAP thiolactone, a self-protected penicillamine derivative, to 10-15 μm diatomaceous earth particles. The efficiencies of both surface silylation and NAP thiolactone attachment were compared between aminosilanes. Diatomaceous earth modified with APTES/NAP yielded the highest levels of silane and NAP attachment and was nitrosated for further evaluation. The chemical modification of DE and retention of particle morphology throughout the derivatization were verified by Fourier Transform infrared spectroscopy (FTIR) and scanning electron microscopy (SEM), respectively. Nitric oxide release over 24 h and total NO content were determined by chemiluminescence. Lastly, the antibacterial and non-cytotoxic properties of this bio-templated NO-releasing diatomaceous earth silica scaffold were evaluated.

Materials and Methods

Materials

Fossil Shell Flour Diatomaceous Earth was purchased from Perma-Guard, Inc. (Bountiful, Utah). 200 proof ethanol was obtained from Decon Labs, Inc. (King of Prussia, Pa.). Toluene and methanol were purchased from Fischer Scientific (Waltham, Mass.). (3-Aminopropyl) triethoxysilane (APTES), L-cysteine hydrochloride monohydrate, 4-Dodecylbenzenesulfonic acid, Ellman's Reagent (5,5'-Dithio-bis-(2-nitrobenzoic acid), DTNB), glycine hydrochloride, 1,4,8,11-tetraazacyclotetradecane (cyclam), t-butyl nitrite, and potassium cyanide (KCN) were purchased from Sigma-Aldrich (St. Louis, Mo.). N-(6-Aminohexyl) aminomethyltriethoxysilane (AHAMTES) and 3-aminopropyldimethylethoxysilane (APDMES) were purchased from Gelest, Inc. (Morrisville, Pa.). Sodium acetate was obtained from EMD Chemicals, Inc. (Gibbstown, N.J.). The bacterial strains *Staphylococcus aureus* (ATCC 6538) and mouse 3T3 cells (ATCC 1658) were originally purchased from American Type Culture Collection (ATCC).

Preparation of N-Acetyl-D-Penicillamine (NAP) Thiolactone

Self-protected NAP thiolactone was synthesized via a slightly modified protocol by Moynihan and Robert [44]. A solution of 5 g NAP in 10 mL pyridine and a separate mixture of 10 mL pyridine and 10 mL acetic anhydride were made. Both solutions were chilled in an ice bath for 1 h before being combined and continuously stirred for 24 hrs. Afterwards, all pyridine in the solution was removed by rotary evaporation at 60° C. to leave behind a small amount of viscous, orange material. This material was dissolved in chloroform and repeatedly washed and extracted with 1 M HCl. The organic layer containing NAP thiolactone was then dried using anhydrous magnesium sulfate subsequently eliminated by filtration. Chloroform was removed under vacuum at room temperature. The collected solid product was washed with hexanes and allowed to dry overnight at room temperature before being stored at 5° C.

SNAP Functionalized Diatomaceous Earth Derivatization

A schematic overview of the SNAP-functionalized diatomaceous earth derivatization is shown in FIG. 1. First, purified DE was amine-functionalized via silyation with APTES, AHAMTES, or APDMES. Next, amine-functionalized particles were reacted with NAP-thiolactone to covalently tether NAP to DE. Finally, NAP-DE was treated with t-butyl nitrite under acidic conditions to form NO-releasing SNAP-DE.

Diatomaceous Earth Purification

To remove trace organic impurities from DE, an aqueous diatomaceous earth suspension was made in a beaker and sonicated. After sonication, dark impurities settled while DE remained suspended. The suspension was decanted into a separate beaker and the process was repeated three times or until all sediment was eliminated. The water in the purified suspension was removed by centrifugation at 3500 rpm for 3 minutes and dried under vacuum.

Surface Silylation

Figure 2:
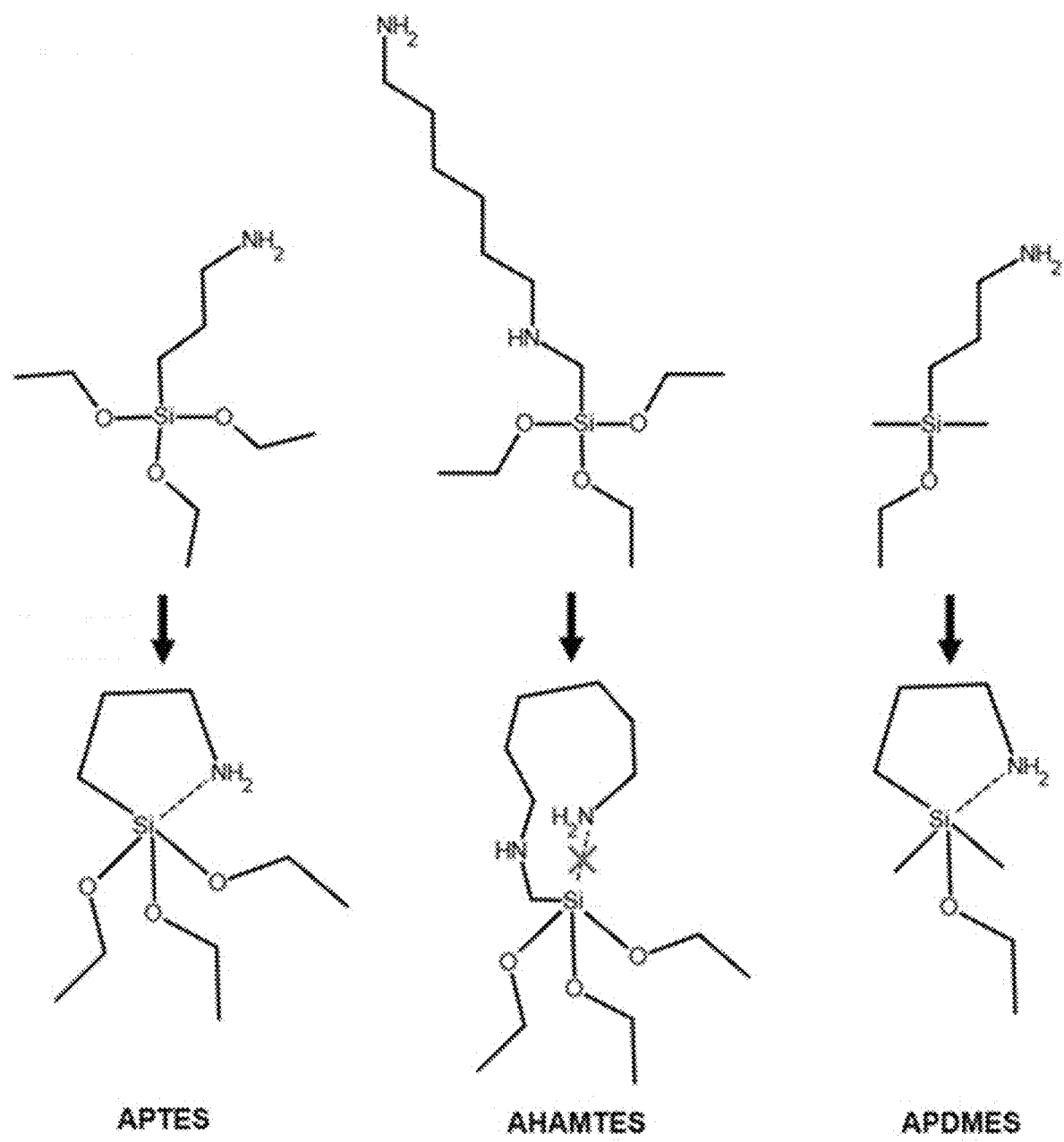
FIG. 2 show traditional structural representations of silylation agents (upper) and conformational representations of silylation agents (lower) during attachment to silica surfaces.

Silylated diatomaceous earth was prepared by refluxing purified DE with one of three aminosilanes (APTES, AHAMTES, APDMES) in toluene for 24 h in accordance with a previously reported protocol (1 g DE: 21.4 mmol aminosilane: 100 mL toluene) [30]. Primary amine-containing silanes (FIG. 2) were selected as crosslinkers because of their ability to promote the NAP-thiolactone ring opening required to tether NAP to aminosilane/DE via an amide bond [45]. After each reflux, the amine functionalized DE products were washed four times with toluene and twice with ethanol before being dried in an oven at 80° C. overnight.

NAP Attachment

NAP-DE was prepared by stirring silylated diatoms with NAP-thiolactone for 24 h in toluene (100 mg silylated DE: 80 mg NAP-thiolactone: 5 mL toluene). Reaction products were washed twice with toluene and dried under vacuum at room temperature for 24 h.

Nitrosation

NAP-DE was added to a solution of 10% methanol, 90% toluene along with 4-Dodecylbenzenesulfonic acid (1 mL DBSA: 100 mg APTES/NAP diatoms) and a molar excess of t-butyl nitrite. The t-butyl nitrite was first cleansed of any copper contaminants by vortexing with an equal volume of 20 mM cyclam. The reaction vessel was shielded from light and agitated for 2 h before its contents were dried at room temperature under vacuum for approximately 30 h.

FQ Primary Amine Quantification

The ATTO-TAG FQ test for primary amines was conducted in accordance with a previously reported protocol [46]. Stock solutions of 10 mM FQ and 10 mM KCN in methanol and water, respectively, were prepared. A working ATTO-TAG FQ solution was created which consisted of 10 μL FQ stock solution, 20 μL of KCN stock solution, 190 μL water, and 5 μL sample. A microplate reader (Biotek, Winooski, Vt.) recorded fluorescence measurements at an excitation of 480 nm and emission maxima at 590 nm. Using the ATTO-TAG FQ solution, a calibration curve of known glycine hydrochloride concentrations was created and the amine content of silylated diatoms was determined.

Ellman's Test for Free Sulfhydryls

Ellman's Reagent, 5,5'-Dithio-bis-(2-nitrobenzoic acid), was used to quantify the free sulfhydryl content of NAP-DE according to a previous protocol [47]. Briefly, a DTNB stock solution (2 mM DTNB, 50 mM NaAc) was used to create a working DTNB solution consisting of 50 μL DTNB stock solution, 100 μL PBS, 840 μL H2O, and 10 μL sample. A UV-Vis spectrophotometer (Thermo Scientific Genesys 10S UV-Vis) recorded absorbance measurements at a previously reported wavelength of 412 nm. Using the DTNB working solution, a calibration curve of known L-cysteine hydrochloride monohydrate concentrations was created and the sulfhydryl content of NAP-DE was determined.

Fourier Transform Infrared Spectroscopy

Fourier transform infrared spectroscopy (FTIR) analysis was used to confirm the presence, absence, and modification of various functional groups throughout the synthesis of SNAP-DE. FTIR spectra of translucent KBr pellets prepared using a 1:100 mass ratio of DE particles:KBr were recorded with a Nicolet 6700 spectrometer (Thermo Electron Corporation, Madison, Wis.). For each sample, 128 scans were obtained at a resolution of 4 $cm^{-1}$ over the wavenumber range of 4000-400 $cm^{-1}$.

Nitric Oxide Release Measurements

Measuring NO release from SNAP-DE was done in real-time via chemiluminescence using a Sievers Nitric Oxide Analyzer (NOA) model 280i (Boulder, Colo.). Samples were weighed and subsequently tested by submersion in 0.01M PBS containing EDTA at 37° C. inside of an amber reaction vessel to protect from light. Nitrogen gas was continuously bubbled and swept from the vessel at a flow rate of 200 mL min-1 to carry the NO being released to the NOA.

Scanning Electron Microscopy and Energy-Dispersive X-Ray Spectroscopy

Scanning electron microscopy (SEM, FEI Teneo, FEI Co.) was used at an accelerating voltage of 5.00 kV to examine the morphology of diatomaceous earth throughout the derivatization. The SEM was equipped with a large detector Energy-dispersive X-ray Spectroscopy (EDS, Oxford Instruments) system used for elemental analysis and mapping of modified diatomaceous earth.

Bacterial Inhibition Test

Bacteria possess a propensity to bind to and form biofilms on polymeric surfaces via secretion of an extracellular matrix. These biofilms eventually calcine, reducing the penetration and thus efficacy of antimicrobial agents such as antibiotics and silver nanoparticles [21, 48]. For this reason, nitric oxide, a free radical naturally bactericidal gas molecule that readily penetrates biofilms, is a potent alternative bactericidal agent.

In the current study, the antibacterial properties of SNAP-DE was tested against gram-positive *Staphylococcus aureus* (*S. aureus*), a common causative agent of blood and nosocomial infections [49-51]. Single isolated colonies of *S. aureus* strains were obtained from a pre-cultured LB agar Petri dish, inoculated in 10 mL of LB medium, and incubated at 37° C., 120 rpm for 14 h. To ensure that the bacteria used in this study were in an actively dividing log phase, the optical density of the culture was measured at a wavelength of 600 nm (OD600) using a UV-vis spectrophotometer (Thermo Scientific Genesys 10S UV-Vis). The bacteria were then separated from the original media and suspended in PBS buffer. This provided the bacteria with an osmotic physiological environment and prevented bacterial proliferation. The separation of cells from the medium was achieved by centrifugation for 7 min at 3500 rpm. The supernatant was discarded, replaced with sterile PBS in order to eliminate traces of medium, and centrifuged for 7 min at 3500 rpm. The supernatant was again discarded and the cells were resuspended in PBS.

The OD600 of the cell suspension in PBS was measured, and adjusted to keep the cell count in the range of 108-1010 colony forming units (CFUs) per mL. The SNAP-DE and unmodified DE were suspended in triplicates (n=3) in 1 mL of PBS-bacteria culture. The bacterial suspension without any DE exposure was taken as a positive control. Before suspension, SNAP-DE was weighed such that 0.8 micro moles of NO were released per mL of PBS/cell solution. This weight was determined by calculating the total NO released per mg of SNAP-DE over a 24-h period under conditions mimicking those of the bacterial suspension. The resulting mixture was incubated at 120 rpm and 37° C. for 24 h. After 24 h, the bacterial suspension was gently agitated with a pipette and serially diluted (10-1 to 10-5) for plating in premade LB agar Petri dishes. The Petri dishes were incubated at 37° C. for 24 h. In parallel, serial dilutions of the bacteria were prepared just before suspending the diatoms in the bacteria culture and plated in LB agar Petri dishes. This verified the consistency of viable cell concentrations between experiments. Post incubation, the CFUs/mg were counted (formula below) to observe the relative bactericidal effect shown by the diatoms and ultimately the relationship between NO release and bactericidal activity.

% Bacterial inhibition =

$$\frac{\left(\frac{CFU}{cm^2} \text{ in control samples} - \frac{CFU}{cm^2} \text{ in test samples}\right) \times 100}{\frac{CFU}{cm^2} \text{ in control samples}}$$

Formazan Based Cell Cytotoxicity Test

WST-*based cell cytotoxicity kit (CCK-8). The cell cytotoxicity kit (CCK-8) (Sigma-Aldrich) provides a standard WST-8 [2-(2-methoxy-4-nitrophenyl)-3-(4-nitrophenyl)-5-(2,4-disulfophenyl)-2H-tetrazolium monosodium salt] based cell viability assay. The CCK-8 test is non-destructive in nature and is more sensitive than other tetrazolium salts such as MTT, XTT, WST-1 and MTS. The number of living cells is directly proportional to the amount of formazan dye (orange color) generated by the interaction of WST-8 with dehydrogenases in the cells and is detected at the absorbance maxima of 450 nm.

Preparation of Leachates

The ISO 10993-5:2009 test for in vitro cytotoxicity was followed to generate leachates from unmodified control DE and SNAP-DE (concentration of 1 mg/mL of medium). This was done by soaking 10 mg of the sterilized SNAP-DE in 10 mL DMEM medium in an amber color vials and incubating for 24 h at 37° C. After 24 h, the extracts were kept in the refrigerator (4° C.) prior to use in the cell culture experiment.

Cell Culture

Mouse Fibroblast cells were used as representative mammalian cells to demonstrate the presence or absence of any potential cytotoxic effect that SNAP-DE might have towards host cells. 3T3 mouse fibroblast cell line (ATCC-1658) was used and leachates were obtained from the biomaterial in accordance with the ISO 10993 standard. A cryopreserved vial was thawed and cells were cultured in 75 cm2 T-flask containing complete DMEM medium with 10% fetal bovine serum (FBS). Additionally, 1% penicillin-streptomycin was added to keep the culture contamination free. The T-flask with cells was incubated at 37° C. in a humidified atmosphere with 5% CO2 over a period of 8 days to allow the formation of a monolayer. The culture medium was replaced intermittently and cells were checked daily for growth and absence of contamination. After the confluence reached above 80%, the cells were detached from the T-flask (trypsinized with 0.18% trypsin and 5 mM EDTA). Finally, the cells were counted under hemocytometer using Trypan blue (dye exclusion method). Around 5000 cell/mL were seeded in each of the wells in a cell culture grade 96 well plate and incubated for 24 h in a humidified incubator with 5% CO2.

Cytotoxicity Test

The manufacture's protocol (Sigma-Aldrich) was followed to perform the cytocompatibility test using a CCK-8 kit on the mouse fibroblast cells. After 24 h of cell culture incubation in a 96 well plate, 10 μL of the leachates from control DE and SNAP-DE were added (n=7) to the cells. The cells were allowed to respond to the leachates during a separate 24 h incubation period inside a cell culture incubator at physiological temperature. After 24 h, 10 μL of the WST-8 solution was added to the resulting solution and incubated for 4 h. In these four h, the dehydrogenase enzyme from the live cells acted upon the WST-8 solution and converted it into an orange color product, formazan, which was measured at 450 nm. The relative viability (%) of the cells as a response to SNAP-DE leach outs was reported relative to the control (without leachate exposure) using the formula below.

$$\% \text{ Cell Viability} = \frac{\text{Absorbance of the test samples}}{\text{Absorbance of the control samples}} \times 100$$

Results and Discussion

Amine Quantification of Functionalized Diatomaceous Earth

The primary amine content of DE post-silyation was quantified to verify the presence of amine-functionalized intermediates and gauge overall reaction efficiencies. Because it is well documented that non-surface bound silanes are readily eliminated by thorough washing, it can be safely assumed that the primary amines detected by FQ belong exclusively to surface bound coupling agents [52-55]. ATTO-TAG FQ reacts with the primary amines of these coupling agents to form a highly fluorescent product detectable to the attomole range [46]. Post-silylation primary amine levels were found to be 1.10±0.17, 0.15±0.01, and 0.11±0.03 μmol/mg for APTES, AHAMTES, and APDMES treated DE, respectively (Table 1).

TABLE 1

| Crosslinker[a] | Amine Content (μmol/mg)[b] | Thiol Content (μmol/mg)[c] | Conversion Ratio (%)[d] |
|---|---|---|---|
| APTES | 1.10 ± 0.17 | 0.0312 ± 0.006 | 2.84 |
| AHAMTES | 0.15 ± 0.01 | 0.0181 ± 0.003 | 12.1 |
| APDMES | 0.11 ± 0.03 | 0.0130 ± 0.001 | 11.82 |

[a]Type of aminosilane used to functionalize the surface of diatomaceous earth particles.
[b]Primary amine content of diatomaceous earth particles after silylation.
[c]Sulfhydryl content of silylated diatomaceous earth after NAP addition.
[d]Ratio between sulfhydryl content after NAP addition and amine content before NAP addition.

Figure 3:
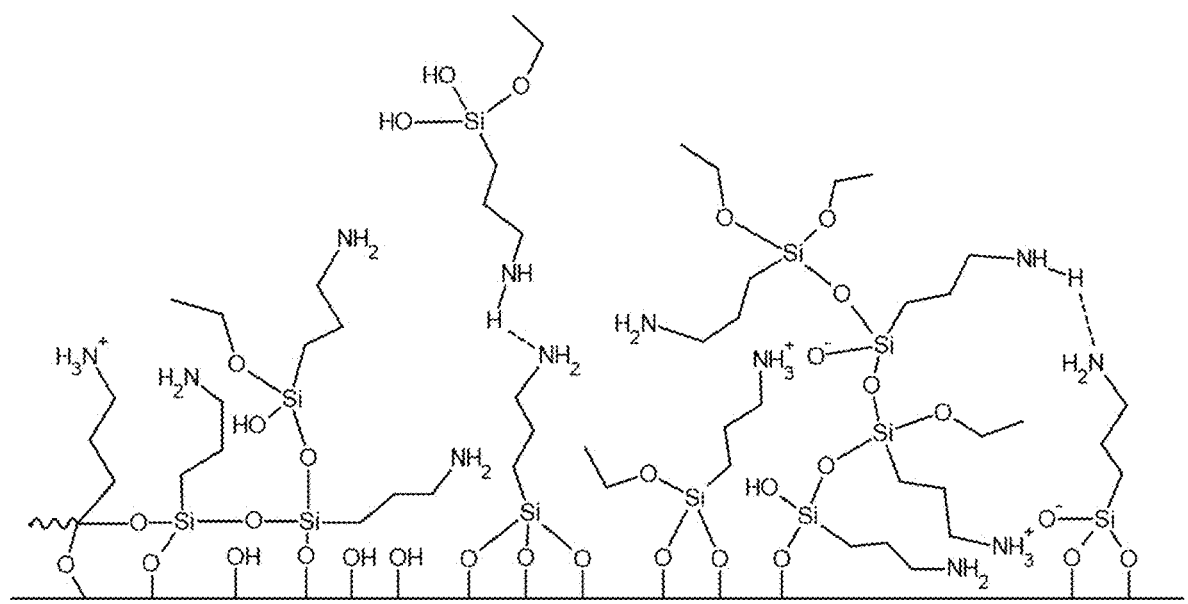
FIG. 3 is a schematic representation of aminosilane attachment and self-polymerization occurring on the diatomaceous earth silica surface.

Interestingly, APTES/DE showed amine levels approximately 7 times higher than AHAMTES/DE and 10 times higher than APDMES/DE derived under the same conditions. The likely explanation for this variance stems from the differing molecular structures, and thus reactivities, of the three aminosilanes. It is widely theorized that aminosilane attachment proceeds via the primary amine catalyzed SN2 exchange reaction between the ethoxy groups of silanes and the oxygens of silanols [52-54]. Because of this, APTES and AHAMTES, which possess three ethoxy groups each, are inherently more reactive than APDMES containing only a single ethoxy group. Three ethoxy moieties allow APTES and AHAMTES to self-polymerize with surface bound and free aminosilanes to form three-dimensional amine rich surface multi-layers (FIG. 3).

While this explains the tendency for APDMES to form only low amine content monolayers, it fails to explain why APTES and AHAMTES, despite their equivalent number of ethoxy groups, result in considerably different amine concentrations. Because aminosilylation relies upon intramolecular primary amine catalysis, it is essential that the terminal amines of APTES and AHAMTES be available to the sites of SN2 exchange [53, 54]. While APTES is believed to form a five-membered cyclic intermediate which places its primary amine adjacent to the site of SN2 exchange, AHAMTES possesses a significantly longer alkyl chain which reduces its ability to undergo a similar intramolecular catalysis (FIG. 2) [53, 54]. This conformational difference reduces the ability of AHAMTES to form high amine content surface coatings [54].

Sulfhydryl Quantification of Diatomaceous Earth

The thiol content of silylated diatomaceous earth after reaction with NAP-thiolactone was determined using Ellman's Reagent (DTNB). DTNB reacts with sulfhydryls to diffuse a yellow product into solution that is quantifiable by UV-vis. Because free thiols arise only after the primary amine-initiated ring opening of NAP-thiolactone, sulfhydryl content serves as a direct indicator of covalent NAP attachment. The sulfhydryl concentrations of APTES, AHAMTES, and APDMES were found to be 0.0312±0.006, 0.0181±0.003, and 0.0130±0.001 μmol/mg, respectively (Table 1).

While these results support the expectation that higher levels of surface bound amines result in increased NAP attachment, a direct proportionality between amine content and subsequent NAP attachment was not observed. Specifically, while one would expect APTES/DE to possess NAP levels 7 times higher than AHAMTES/DE and 10 times higher than APDMES/DE (based on amine content), APTES/DE instead demonstrated 1.7 and 2.4 times more NAP attachment than AHAMTES/DE and APDMES/DE, respectively. A closer examination of these results reveals that the percentages of surface amines tethered to NAP-thiolactone were 2.84, 12.1, and 11.8% for APTES, AHAMTES, and APDMES, respectively.

Because the thickness of aminosilane layers is the most meaningful difference between crosslinkers employed in this work, lower amine conversion ratios for APTES multilayers suggests that the deposition of aminosilane coupling agents past monolayer thicknesses improves NAP attachment only marginally. As stated previously, it has been suggested that APTES routinely forms nonuniform, highly dense, interconnected silane networks (FIG. 3) [52-54, 56]. In such an environment, NAP-thiolactone, with its highly-substituted ring structure, likely experiences steric congestion toward nucleophilic attack [45]. Accordingly, NAP-thiolactone ring opening is unlikely to occur within the interconnected silane network believed to be present on the diatomaceous earth surface. However, penetration is not impossible and although the aminosilane multilayers of APTES resulted in a lower overall conversion ratio, an increase in the sheer quantity of NAP attachment was observed.

While steric hindrance explains differences in amine conversion between dense multilayers of APTES and thin layers of AHAMTES and APDMES, relatively low conversion ratios for even thin aminosilane layers suggest that more factors are at play in NAP-thiolactone binding than sterics alone. Similarly low amine conversions were observed by Frost et al. when tethering NO-releasing groups to amine-modified fumed silica particles [30]. Future work will examine explanations for this to further optimize reaction efficiencies. Because the goal of this work was to develop diatomaceous earth with maximal NO-release capacity, APTES/NAP, with its high quantity of nitrosatable sulfhydryl groups, was selected for further analysis.

Fourier Transform Infrared Spectroscopy

Figure 4:
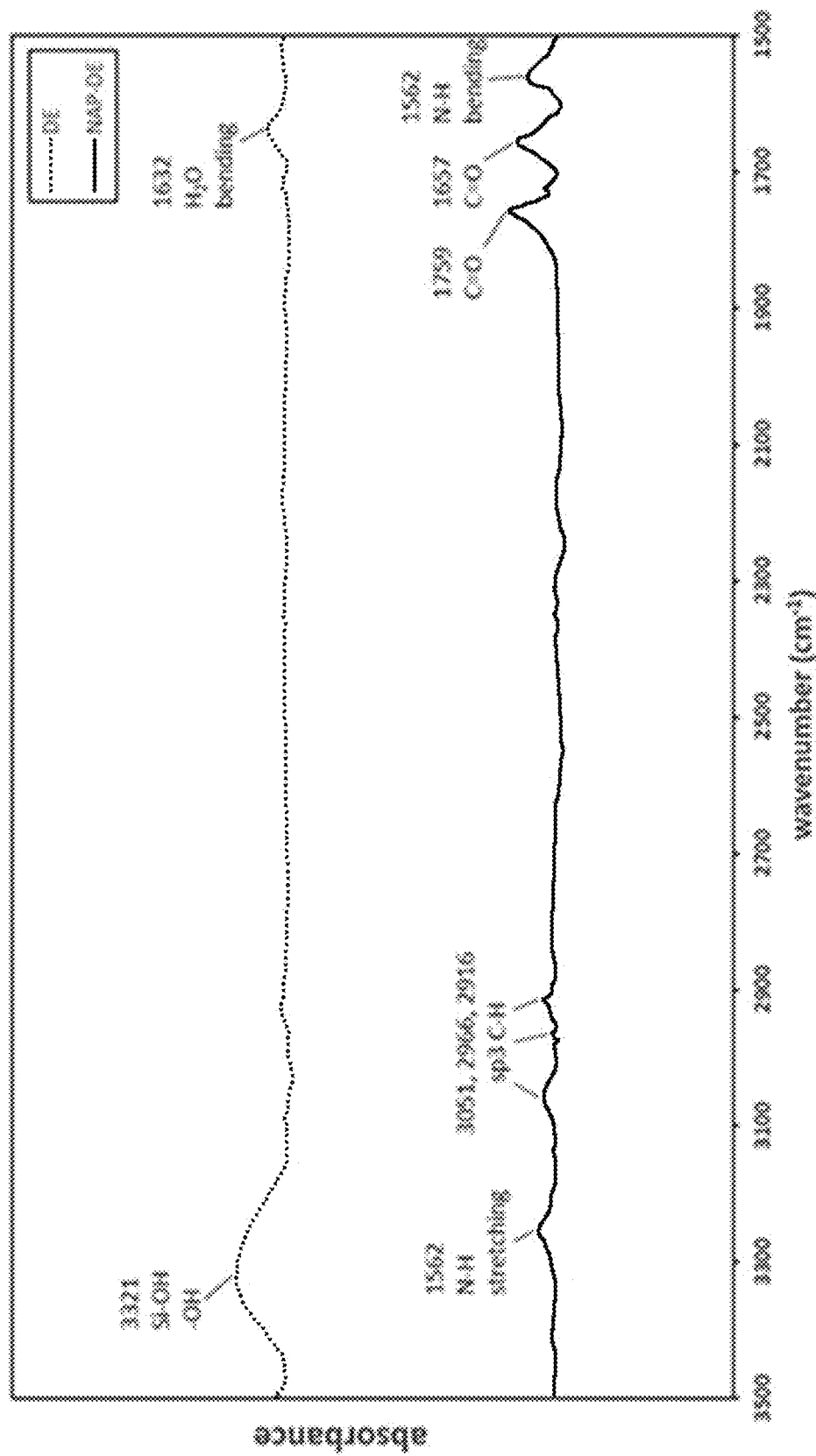
FIG. 4 shows Fourier-transform infrared spectra of unmodified diatomaceous earth (upper curve) and N-acetyl-penicillamine modified diatomaceous earth (lower curve).
Figure 5:
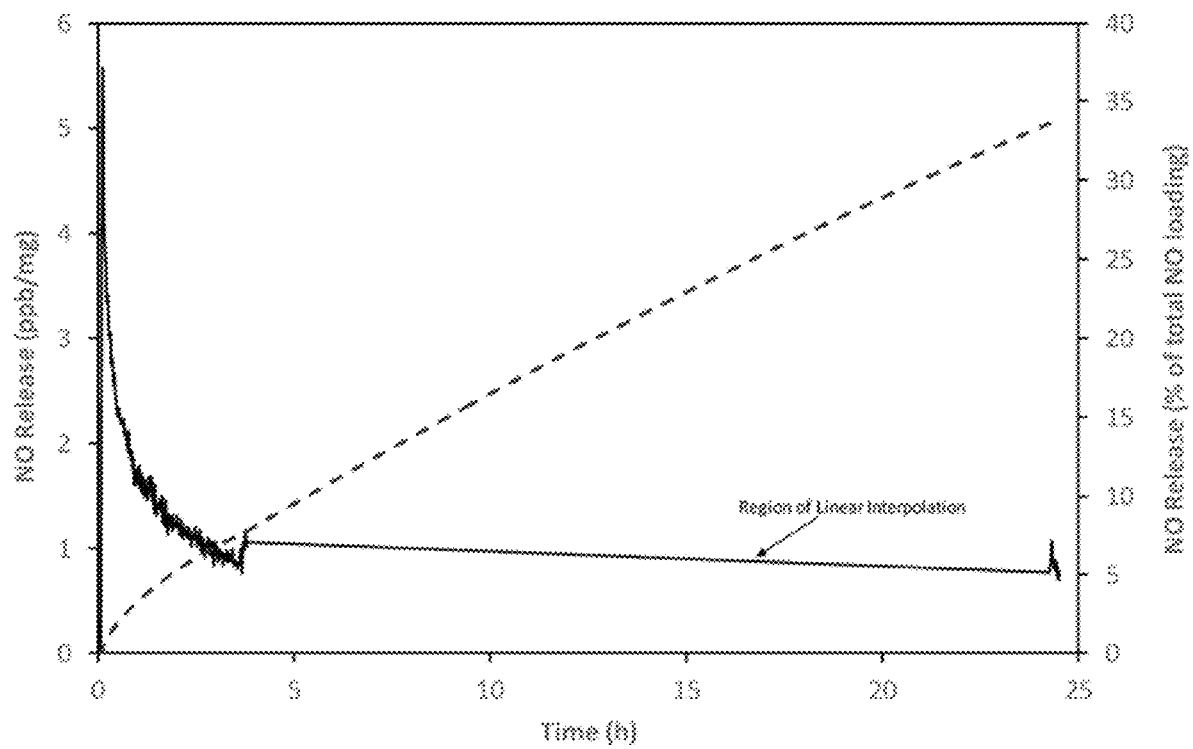
FIG. 5 shows a representative 24-hour nitric oxide release profile for S-nitroso-N-acetyl-penicillamine modified diatomaceous earth (SNAP-DE) as both an instantaneous parts per billion per mg SNAP-DE (PPB/mg) value and cumulative percentage. Because SNAP-DE nitric oxide-release levels plateaued quickly, this profile was prepared by linearly interpolating between steady-state data recorded at the beginning and end of the 24-hour period.

FTIR spectra of unmodified-DE and NAP-DE are shown in FIG. 4, and indicate successful chemical modification of diatomaceous earth. In the unmodified-DE spectrum, the vibration observed at 3321 cm$^{-1}$ corresponds with both the Si—OH bonds abundant on the silica surface and the —OH bonds of water physically absorbed to the silica surface. In the same spectrum, the band at 1632 cm$^{-1}$ is consistent with bending vibrations of surface bound H2O. The disappearance of the broad peak at 3321 cm$^{-1}$ in the NAP-DE spectrum indicates the elimination of Si—OH groups and physically absorbed water upon silylation with APTES and NAP attachment. Moreover, the presence of conjugated amides consistent with the structure of NAP-DE in this spectrum is suggested by carbonyl vibrations at 1759 cm$^{-1}$ and 1657 cm-1, N—H stretching at 3251 cm$^{-1}$ and 3197 cm$^{-1}$, and N—H bending at 1562 cm-1. Sp3 C—H bonds consistent with the alkyl chain of APTES and methyl groups in NAP are seen in subtle vibrations at 3051 cm-1, 2966 cm$^{-1}$, and 2916 cm$^{-1}$.

Nitric Oxide Content and Release Kinetics of SNAP-DE

Chemiluminescence, one of most popular means of quantifying nitric oxide release from materials, was used to determine the total NO content and release kinetics of SNAP-functionalized diatomaceous earth (SNAP-DE). Total NO release from SNAP-DE was found to be 0.0372±0.00791 µmol/mg using alternating injections of 0.25 M copper (II) chloride and ascorbic acid. This value of NO loading is within range of the sulfhydryl levels quantified by Ellman's Assay (0.0312±0.0061 µmol/mg), indicating efficient nitrosation. Nitric oxide release of 0.0372±0.00791 µmol/mg attained through the covalent attachment of NO donor minimizes the chance of toxic NO levels occurring when SNAP-modified DE is substituted for traditional DE in applications requiring bulk quantities of material. Furthermore, because targeted NO release levels vary greatly across applications, the ability to fine-tune NO flux by modulating the mass of SNAP-DE incorporated into materials is a tremendous asset.

Figure 6A:
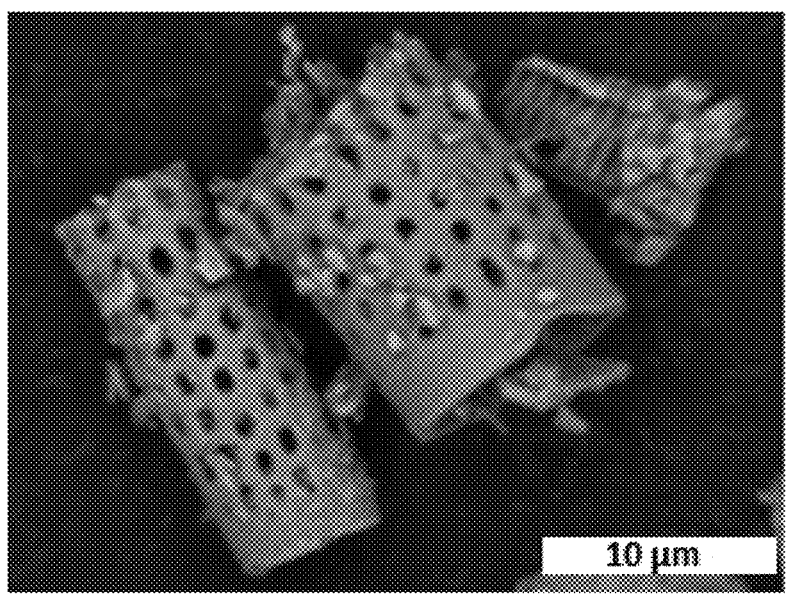
FIGS. 6A-6B show scanning electron microscope images of diatomaceous earth (FIG. 6A) before and (FIG. 6B) after covalent S-nitroso-N-acetyl-penicillamine attachment.
Figure 6B:
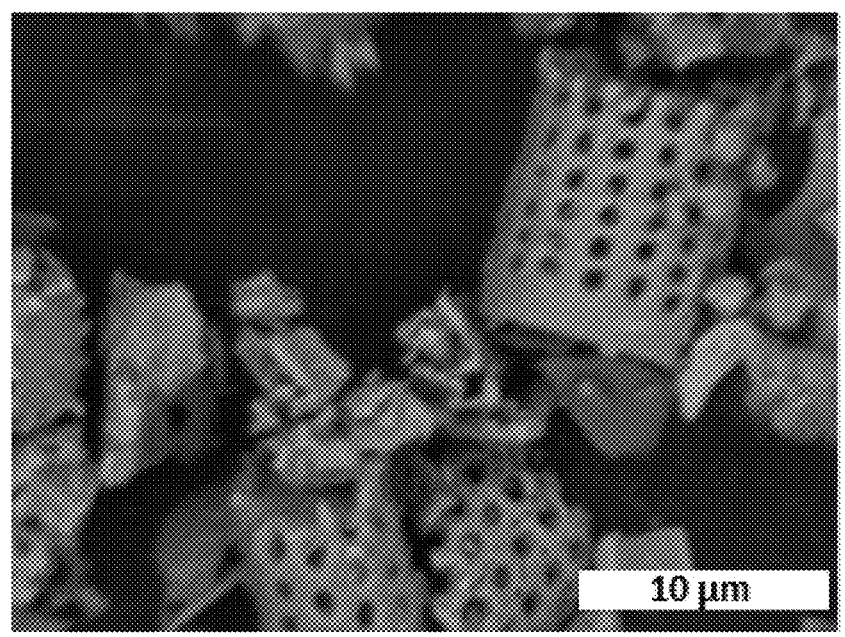
Figure 7A:
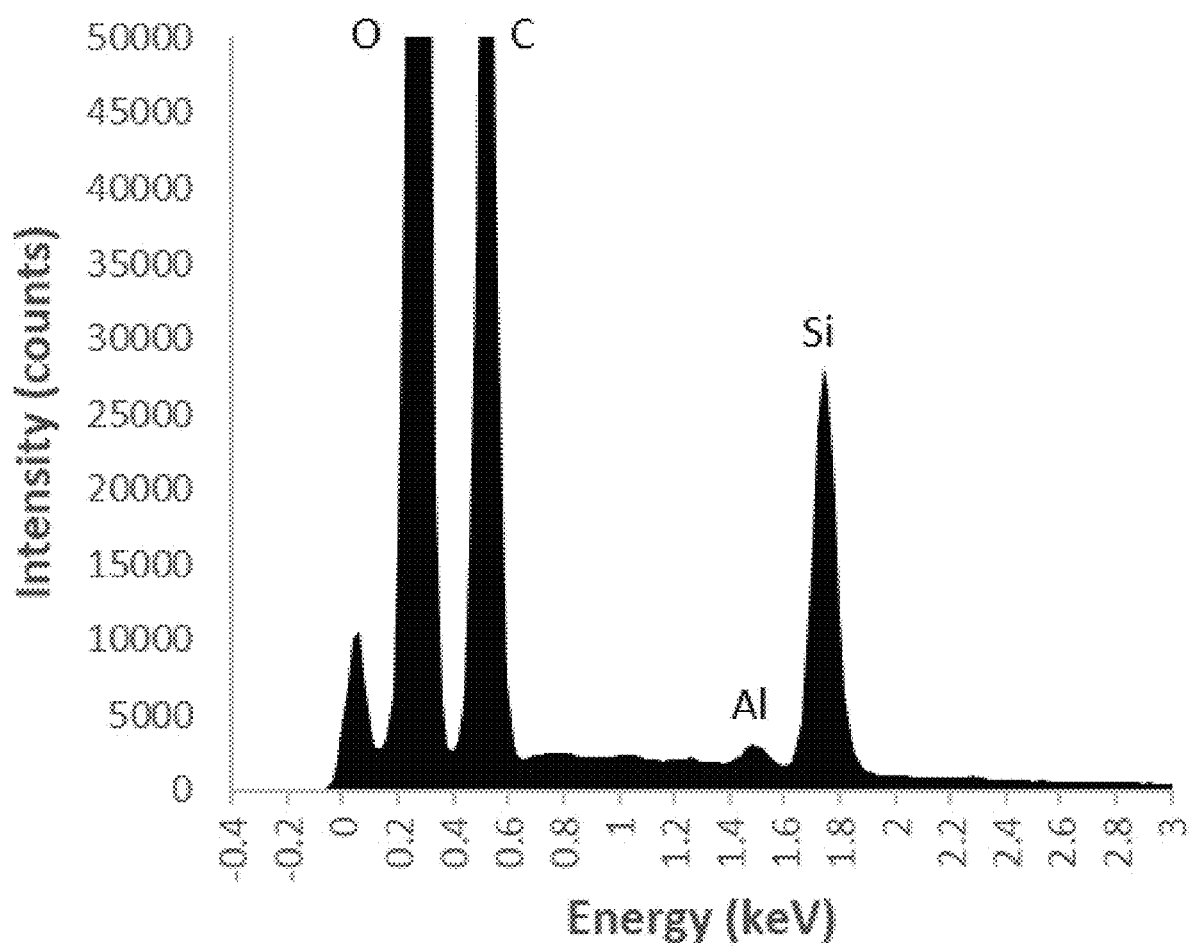
FIGS. 7A-7F show energy dispersive X-ray spectra of (FIG. 7A) unmodified diatomaceous earth and (FIG. 7B) S-nitroso-N-acetyl-penicillamine modified diatomaceous earth (SNAP-DE)
Figure 7B:
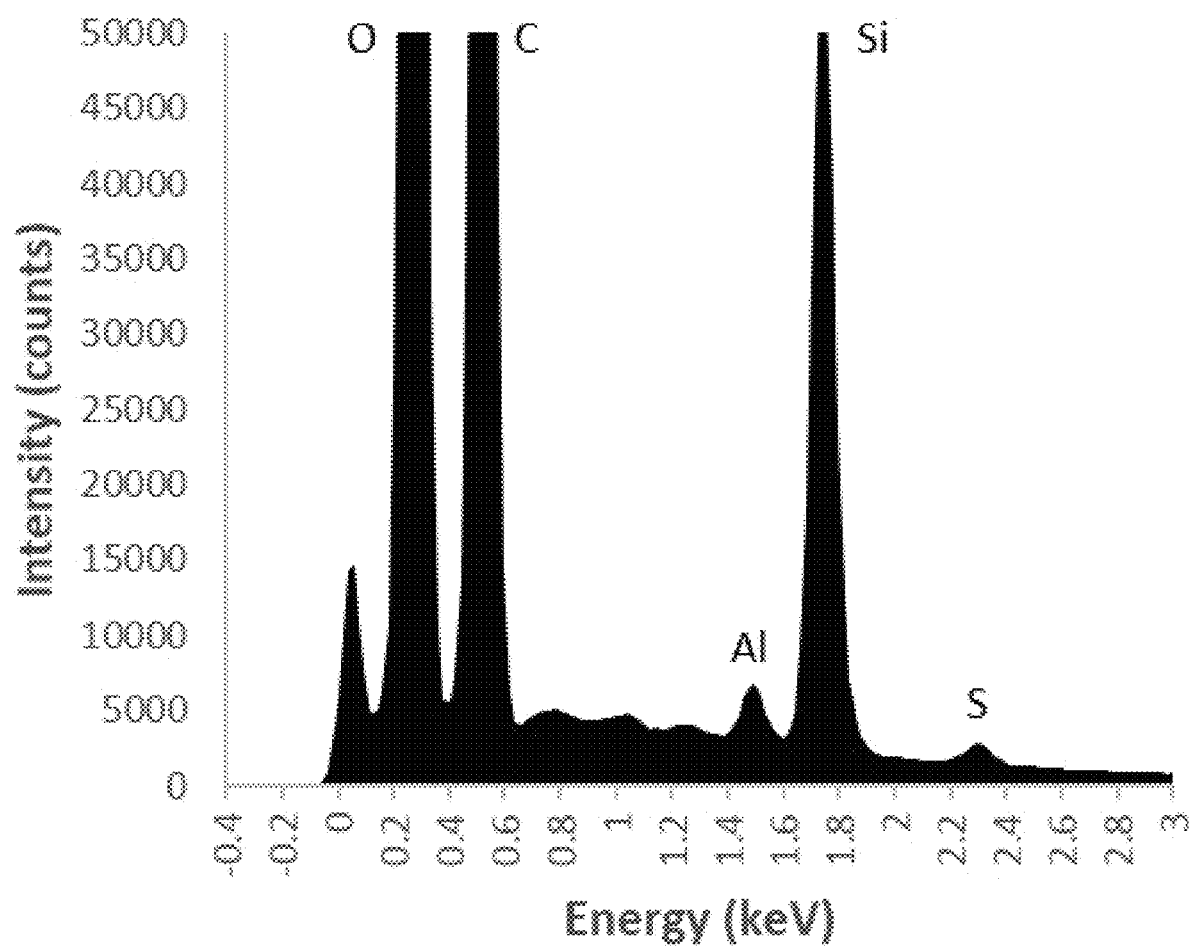
Figure 7C:
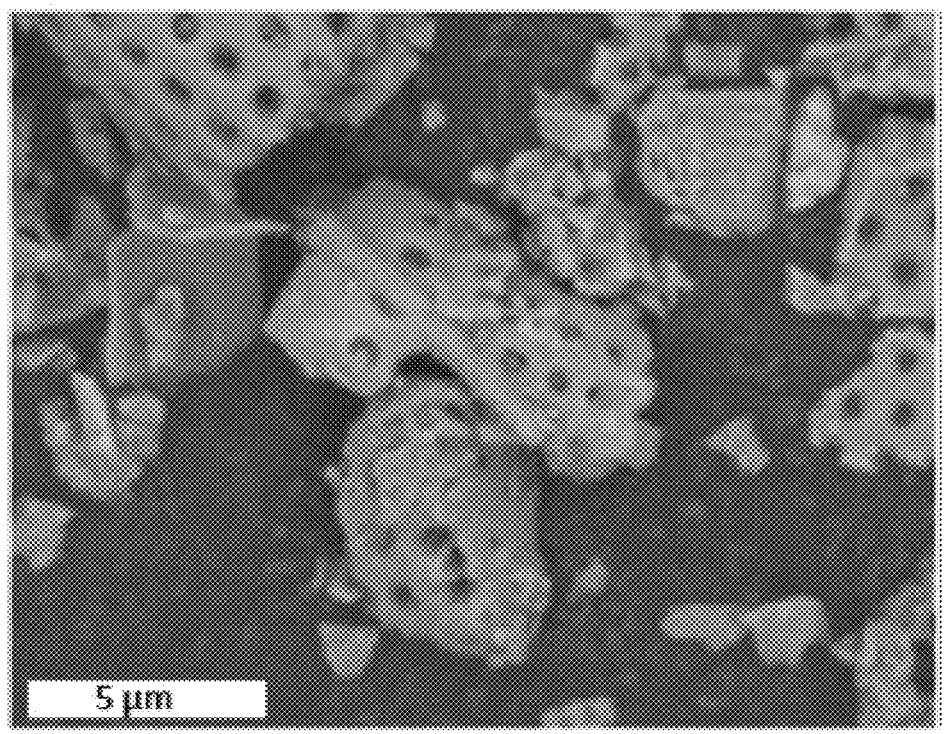
Figure 7D:
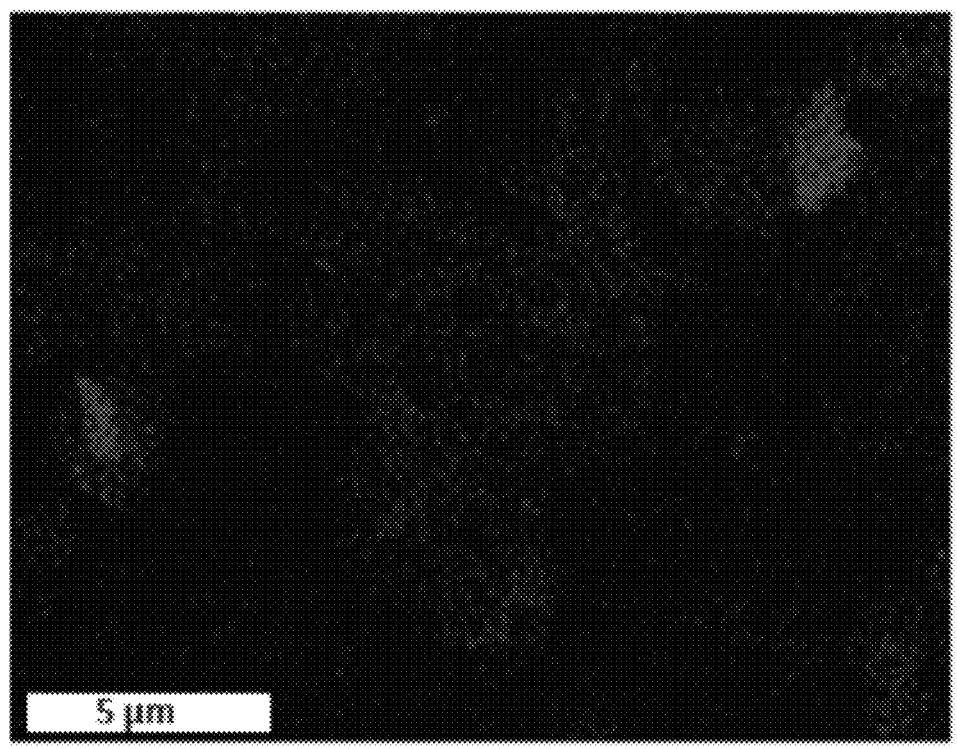
Figure 7E:
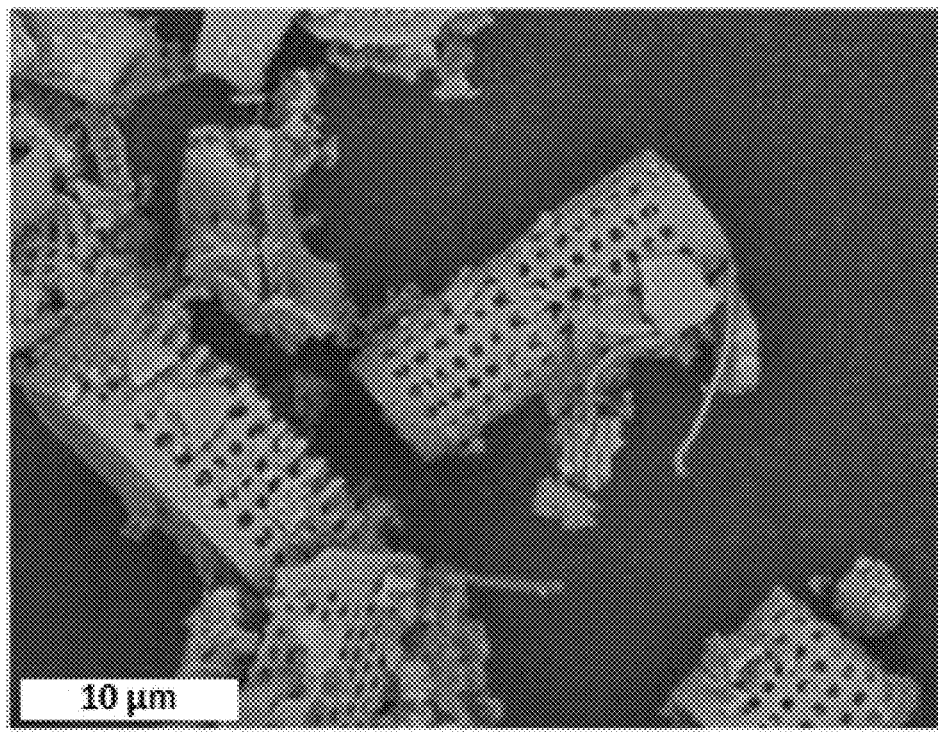
Figure 7F:
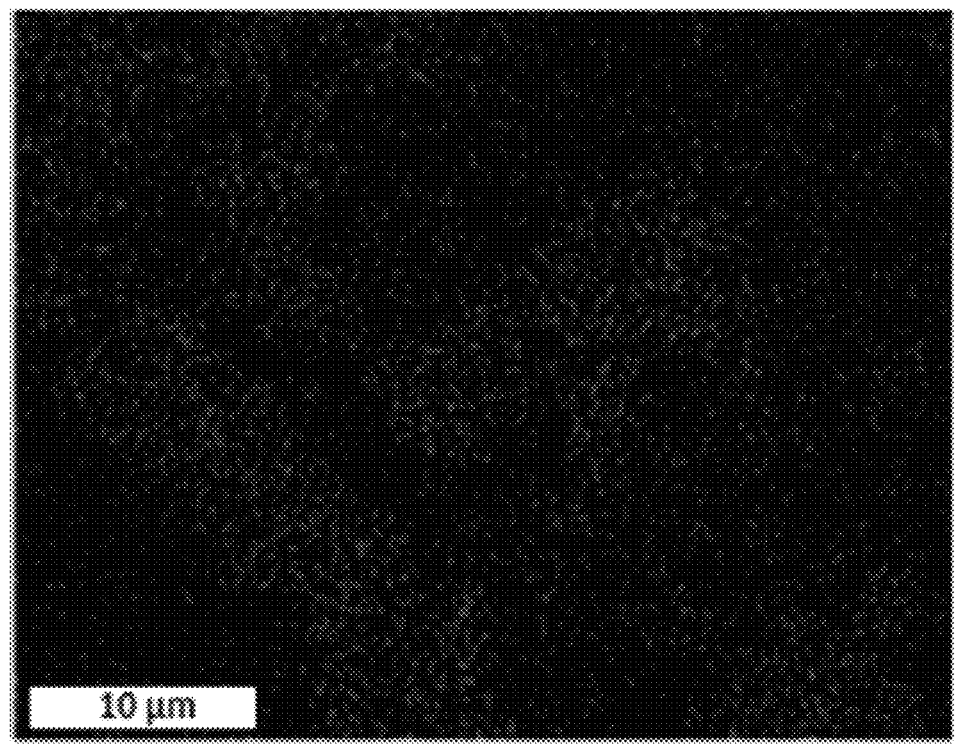

Physiological conditions were chosen for NO release testing to mimic the in vivo conditions of biomedical applications and for facile comparison with previously reported NO-releasing particles. FIGS. 6A-6B illustrate the nitric oxide release from SNAP-DE as both an instantaneous value and a cumulative percentage of total NO loading over a 24-h period. Notably, the NO release half-lives of SNAP-DE routinely exceeded 24 h, significantly improving upon the half-lives of previously reported diazeniumdiolate-based silica particles (6 min-12 h) [31, 32, 34]. Sustained release of moderate levels of NO offers a unique combination of NO release kinetics and loading which expands upon the applications for currently existing NO technology, particularly in the areas of platelet inhibition and bacteria killing [57, 58]. Because the NO release levels of SNAP-DE plateaued shortly after addition to the reaction chamber, a 24-h release profile was prepared by linearly interpolating between steady-state data recorded at the beginning and end of a 24-h period. Nitric oxide-releasing DE particles offer a naturally-based, bio-inspired, and tunable (by varying the amount of incorporated SNAP-DE) means of incorporating NO into polymers, hydrogels, pastes, and creams.

Scanning Electron Microscopy and Energy-Dispersive X-Ray Spectroscopy

SEM images of diatomaceous earth seen in FIGS. 6A-6B illustrate the retention of particle morphology throughout the SNAP-DE derivatization. Morphological conservation is imperative to the maintenance of diatomaceous earth's uniqueness as an NO donor system. In the past, fumed silica has been used in the derivatization of NO-releasing silica particles [30, 31]. A known issue with fumed silica, however, is its aggregation into course, irregular clusters during pyrolytic production [59]. These irregularities render particle morphology highly unpredictable and conversion to an NO-releasing product with consistent release kinetics challenging [30, 31]. The diatomaceous earth used in this work, however, is made mostly of discrete centric diatom species 4-6 µm in diameter and 10-20 µm in length possessing large openings on either end and highly-order rows of 400-500 nm pores [60]. Such an ordered, porous structure would be extremely difficult to reproduce by the synthetic means employed in previous studies and affords diatomaceous earth unique physical properties invaluable to the fields of biosensing, filtration, immunoprecipitation, microfluidics, nanofabrication, protein catalysis, and drug delivery [32, 34, 58, 60].

Virtually all previously reported NO-releasing silica particles have been nonporous and on the nanoscale [30-32, 34, 58]. Although mesoporous NO-releasing silica particles have been described by Soto et al., the diatomaceous earth particles highlighted herein feature systematic pore and particle structures hundreds of times larger than those reported previously [34]. Because porosity and size have been shown to directly affect the loading efficiency, release kinetics, and degradation rates of therapeutic materials, such a substantial divergence from previous particle morphologies stands to broaden the application range and utility of NO-releasing silica [61]. Specifically, porous silicon microparticles are being explored as "mother ships" capable of carrying therapeutic payloads such as nanoparticles, proteins, enzymes, drugs, and genes [62].

EDS spectra of both unmodified-DE and SNAP-DE, along with chemical mapping of elemental sulfur can be seen in FIGS. 7A-7D. Because SNAP is the only sulfur-containing material used in the synthesis of SNAP-DE, the presence of sulfur in modified DE samples serves as a direct indicator of SNAP presence. The EDS spectra of SNAP-DE clearly indicates the appearance of an elemental sulfur peak and thus the incorporation of SNAP into the sample. Sulfur mapping of SNAP-DE substantiates and visually complements this finding by showing high concentrations of elemental sulfur in the same location as SNAP-DE particles.

Bactericidal Properties of SNAP-DE

Figure 8A:
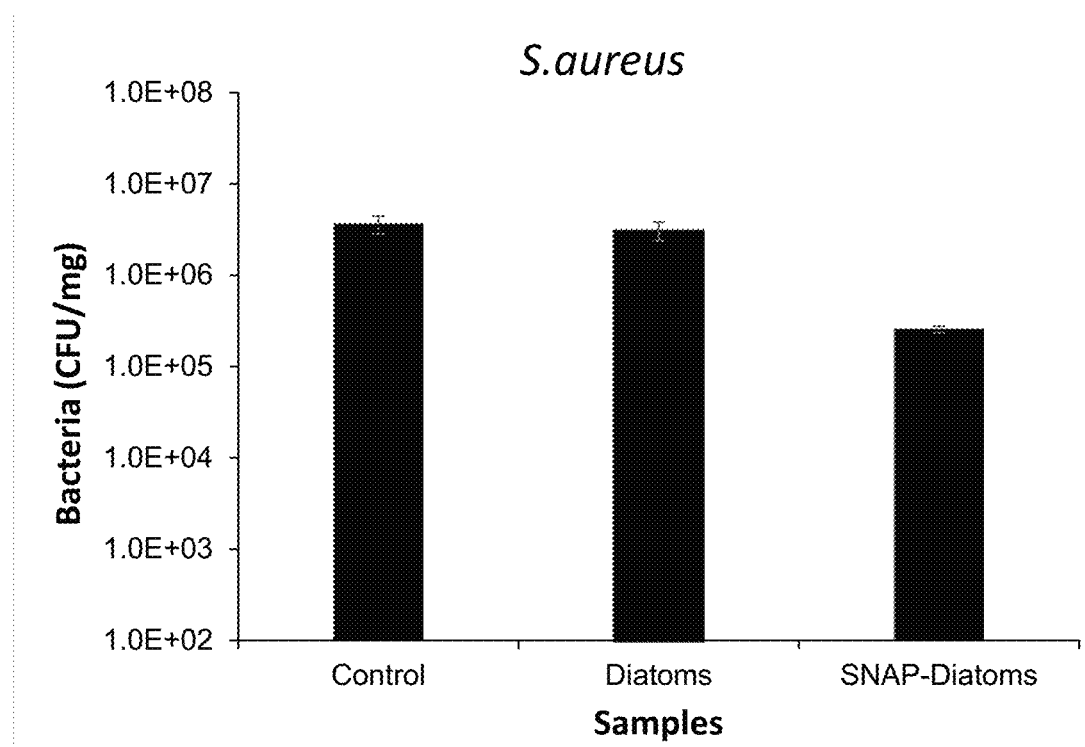
FIGS. 8A-8B show a graphical comparison of the viable bacterial colony forming units per mg (CFU/mg) for unmodified diatomaceous earth and SNAP-diatomaceous earth after 24 hours of exposure. Bacteria grown without exposure to either diatomaceous earth or S-nitroso-N-acetyl-penicillamine modified diatomaceous earth (SNAP-DE) were used as a control. As a proof of concept, gram positive S. aureus, one of the major causal agents of biofilm formation and nosocomial infections, was used to test the antibacterial property of SNAP-DE. The bactericidal nature of nitric oxide killed the bacteria on a logarithmic scale (FIG. 8A) and resulted in 92.95±2.6% of reduction (FIG. 8B).
Figure 8B:
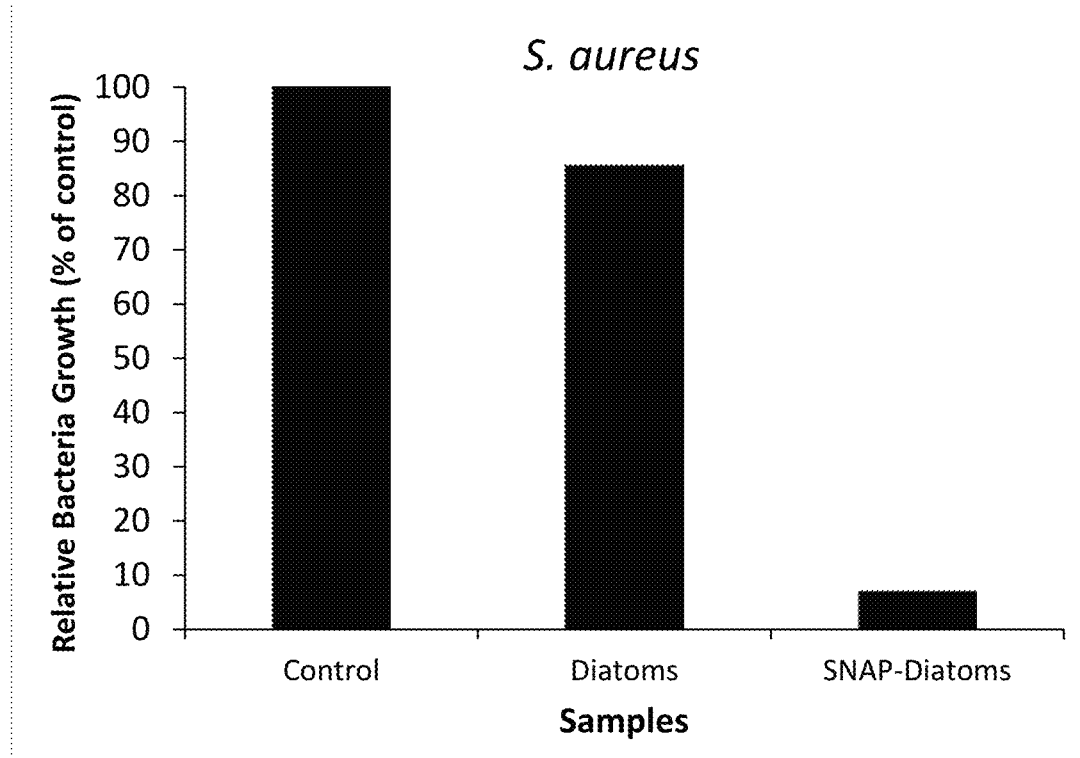

The successful development of new-age therapeutic biomaterials hinges, in large part, on their antibacterial properties. *S. aureus*, a major source of hospital acquired infections, forms a matrix on substrate surfaces and often results in biofilms resistant to antimicrobial agents such as antibiotics and silver nanoparticles [63-65]. Accordingly, *S. aureus* was selected in this study to serve as a proof of concept evaluation of the antibacterial properties of SNAP-DE in biomaterial applications. Unmodified DE showed a slight reduction in bacterial CFUs as compared to the control, whose bacterial reduction was enhanced to the log scale in the presence of SNAP (FIGS. 8A-8B). The NO releasing SNAP-DE showed 92.95±2.6% bacterial reduction as compared to the positive control sample (without DE or SNAP-DE). Because the presence of nitric oxide-releasing moieties marks the only difference between SNAP-DE and positive and DE controls, bacterial inhibition is attributable to the toxic effects of NO against bacteria alone.

Nitric oxide kills bacteria via non-specific mechanisms which involve thiol and amine nitrosation in the extracellular matrices of bacteria, DNA cleavage, lipid peroxidation and tyrosine nitrosation [66]. Moreover, unlike antibiotics and silver nanoparticles, bacterial resistance to NO is unlikely to develop due to the molecule's rapid and non-specific action [6, 67, 68]. In the past, our group and others have shown the antimicrobial effects of NO releasing biomaterials against P. aureginosa, S. aureus, E. coli, A. baumanni, S. aureus, E. coli, L. monocytogenes, and E. faecalis [5, 27, 69-72]. In many of these studies, NO donors were either blended or chemically linked to polymers while bacterial growth and inhibition was observed on the surface. The previous success of NO against the aforementioned bacteria, along with the bactericidal effects of SNAP-DE shown directly in this work, suggest that SNAP-DE can be an efficacious and versatile biomaterial both in its own right and as an additive to currently existing technologies. This work marks the first time an NO donor has been covalently linked to diatomaceous earth to form a next-generation NO-delivery scaffold of natural origin.

Cytotoxic Effects of SNAP-DE

Figure 9:
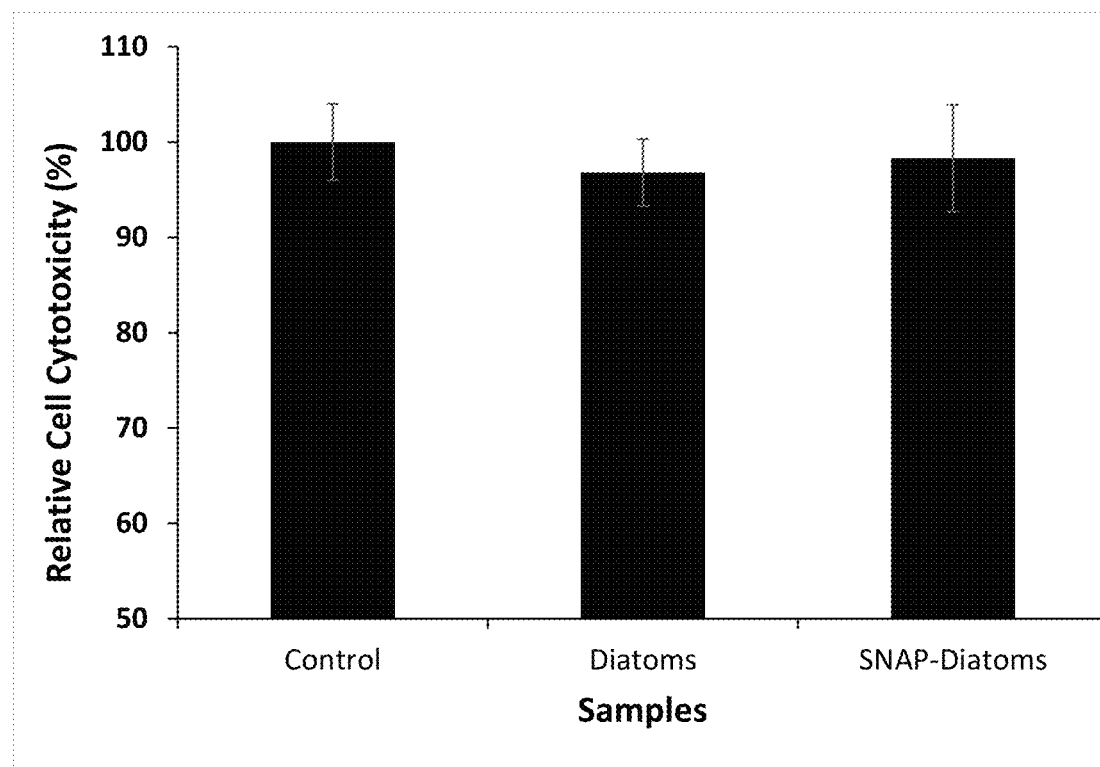
FIG. 9 shows the cytotoxic potential of S-nitroso-N-acetyl-penicillamine modified diatomaceous earth (SNAP-DE) leachates in solution and was tested on 3T3 mouse fibroblast cells using a WST-8 dye based CCK-8 kit. Cells exposed to the leachates from diatomaceous earth and SNAP-DE demonstrated cell viabilities similar to those of control cells not exposed to leachates.

The in vitro cytotoxicity assay marks a proof of concept evaluation of the material's potential biocompatibility of a given biomaterial. The current study was performed per ISO standards for cytotoxicity using a WST-8 dye based CCK-8 kit (Sigma-Aldrich). Although research groups in the past have shown the antibacterial properties of antibiotics, silver nanoparticles, and NO-releasing materials the toxic nature of these materials was either not tested or was found to be cytotoxic to mammalian cells [63, 65, 73-77]. Therefore, evaluating the cytotoxicity of SNAP-DE in addition to its antibacterial properties, was a major objective of this work. Mouse fibroblast cells were exposed to 10 µL of SNAP-DE material (1 mg/mL). Results for the test indicated that SNAP-DE possessed levels of fibroblast cell viability similar to those of the control (cells in the cell culture well without any material). No significant (n=7) differences were found in the cytotoxicity analysis in the presence or absence of SNAP (FIG. 9). In addition to the observed viability, the medium color remained red (phenol red indicator) showing that the metabolism of the fibroblast cells did not turn to cause an acidic pH.

These results are consistent with previous studies demonstrating the cytocompatibility of both SNAP and diatomaceous earth. Specifically, diatomaceous earth has been utilized in personal hygiene and dietary applications for decades without issue and SNAP has been shown to be non-cytotoxic, biocompatible, and hemocompatible both in vivo and in vitro [4, 60, 78, 79], [Cu-SNAP]. Moreover, the major degradation product of SNAP, NAP, has been used in the safe treatment of medical conditions at doses of 2-4 g/day [14]. A number of studies have evaluated the toxicity of silica particles synthesized by various means, often with conflicting results [61, 80, 81]. A general consensus, however, exists that high concentrations of silanol functionalities ($\equiv$SiOH) on silica surfaces leads to increased toxicity. It is theorized that surface silanols compromise cell integrity by hydrogen bonding to key membrane components and/or dissociating above pHs of 2-3 to electrostatically interact with positively charged tetraalkylammonium-containing phospholipids [81]. This silanol associated toxicity stands to be minimized in SNAP-DE through high particle porosity and the encapsulation of silanol groups with amine layers. Porosity reduces the solid fraction of modified silica particles and thus the number of silanols available to negatively affect cell membranes [80-82]. Furthermore, the coverage of silaceous diatomaceous earth with aminosilanes likely forms a protective layer that limits cell accessibility to unreacted surface silanols [82]. These properties are in contrast to previously reported and largely non-porous NO-releasing silica particles formed by co-condensation methods that homogeneously incorporate silanols throughout particles [32, 34, 58].

The lack of an observed SNAP-DE toxicity toward mammalian cells and tissue allows for flexibility in testing the material beyond the concentrations used in this study. Overall, SNAP-DE presents a tunable NO delivery vehicle with effective antibacterial and non-cytotoxic properties suitable for graduation to in vivo animal models. A more comprehensive study of SNAP-DE's cytotoxic properties at higher concentrations both in vitro and in vivo will be carried out in the future to prove the preclinical potential of SNAP-DE.

CONCLUSION

In this work, the synthesis and characterization of bio-templated mesoporous nitric oxide-releasing diatomaceous earth was described for the first time. By quantifying primary amine and thiol groups present on the surface of functionalized DE, APTES was shown to maximize NAP attachment and thus NO loading. FTIR and EDS indicated successful modification of DE through the appearance of functional groups and atoms consistent with those of SNAP. SEM confirmed the retention of diatomaceous earth's unique morphology throughout the synthesis. Successful SNAP tethering was further demonstrated via real-time chemiluminescence measurement of NO. Lastly, SNAP-DE particles were shown to reduce bacterial colonies without negatively affecting mammalian cells. The results of this study suggest a promising new bio-templated NO donor system which can be leveraged in applications throughout the biomedical arena.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

REFERENCES

1. Haitham, A.-S. D. and A. Ferro, S-Nitrosothiols: a class of nitric oxide-donor drugs. Clinical science, 2000. 98(5): p. 507-520.
2. Butler, A. R. and D. L. H. Williams, The physiological role of nitric oxide. Chemical Society Reviews, 1993. 22(4): p. 233-241.
3. Ignarro, L. J., et al., Endothelium-derived relaxing factor produced and released from artery and vein is nitric oxide. Proceedings of the National Academy of Sciences, 1987. 84(24): p. 9265-9269.
4. Goudie, M. J., et al., Characterization of an S-nitroso-N-acetylpenicillamine-based nitric oxide releasing polymer from a translational perspective. International Journal of Polymeric Materials and Polymeric Biomaterials, 2016. 65(15): p. 769-778.

5. Pant, J., et al., Tunable nitric oxide release from S-nitroso-N-acetylpenicillamine via catalytic copper nanoparticles for biomedical applications. ACS Applied Materials & Interfaces.
6. Bogdan, C., Nitric oxide and the immune response. Nature immunology, 2001. 2(10): p. 907-916.
7. Lancaster, J., A tutorial on the diffusibility and reactivity of free nitric oxide. Nitric Oxide, 1997. 1(1): p. 18-30.
8. Brisbois, E. J., et al., Long-term nitric oxide release and elevated temperature stability with S-nitroso-N-acetyl-penicillamine (SNAP)-doped Elast-eon E2As polymer. Biomaterials, 2013. 34(28): p. 6957-6966.
9. Wang, P. G., et al., Nitric oxide donors: chemical activities and biological applications. Chemical Reviews, 2002. 102(4): p. 1091-1134.
10. Yamamoto, T. and R. J. Bing, Nitric oxide donors. Proceedings of the Society for Experimental Biology and Medicine, 2000. 225(3): p. 200-206.
11. Vaughn, M. W., L. Kuo, and J. C. Liao, Effective diffusion distance of nitric oxide in the microcirculation. American Journal of Physiology-Heart and Circulatory Physiology, 1998. 274(5): p. H1705-H1714.
12. Carpenter, A. W. and M. H. Schoenfisch, Nitric oxide release: Part II. Therapeutic applications. Chemical Society Reviews, 2012. 41(10): p. 3742-3752.
13. Frost, M. C., M. M. Reynolds, and M. E. Meyerhoff, Polymers incorporating nitric oxide releasing/generating substances for improved biocompatibility of blood-contacting medical devices. Biomaterials, 2005. 26(14): p. 1685-1693.
14. Stokes, G., et al., New Agent in the Treatment of Cystinuria: N-acetyl-D-penicillamine. British medical journal, 1968. 1(5587): p. 284.
15. Goudie, M. J., et al., Characterization and in vivo performance of nitric oxide-releasing extracorporeal circuits in a feline model of thrombogenicity. Journal of Biomedical Materials Research Part A, 2016.
16. Singha, P., J. Locklin, and H. Handa, A Review of the Recent Advances in Antimicrobial Coatings for Urinary Catheters. Acta Biomaterialia, 2016.
17. Brisbois, E. J., et al., Improved hemocompatibility of silicone rubber extracorporeal tubing via solvent swelling-impregnation of S-nitroso-N-acetylpenicillamine (SNAP) and evaluation in rabbit thrombogenicity model. Acta biomaterialia, 2016. 37: p. 111-119.
18. Yu, J., et al., The immobilization of a direct thrombin inhibitor to a polyurethane as a nonthrombogenic surface coating for extracorporeal circulation. Journal of Materials Chemistry B, 2016. 4(13): p. 2264-2272.
19. Koh, A., et al., Fabrication of nitric oxide-releasing polyurethane glucose sensor membranes. Biosensors and Bioelectronics, 2011. 28(1): p. 17-24.
20. Alam, A., et al., Study of Polydiacetylene-Poly (Ethylene Oxide) Electrospun Fibers Used as Biosensors. Materials, 2016. 9(3): p. 202.
21. Pant, J., et al., Nitric oxide-releasing polyurethanes. Advances in Polyurethane Biomaterials, 2016: p. 417.
22. Sundaram, J., et al., Antimicrobial and Physicochemical Characterization of Biodegradable, Nitric Oxide-Releasing Nanocellulose-Chitosan Packaging Membranes. Journal of agricultural and food chemistry, 2016. 64(25): p. 5260-5266.
23. Masters, K. S. B., et al., Effects of nitric oxide releasing poly (vinyl alcohol) hydrogel dressings on dermal wound healing in diabetic mice. Wound Repair and regeneration, 2002. 10(5): p. 286-294.
24. Doxey, R., Nitric Oxide Releasing Pharmaceutical Compositions. 2013, Google Patents.
25. Backlund, C., et al., Kinetic-dependent killing of oral pathogens with nitric oxide. Journal of dental research, 2015. 94(8): p. 1092-1098.
26. Carpenter, A. W., et al., Influence of scaffold size on bactericidal activity of nitric oxide-releasing silica nanoparticles. ACS nano, 2011. 5(9): p. 7235-7244.
27. Brisbois, E. J., et al., Optimized polymeric film-based nitric oxide delivery inhibits bacterial growth in a mouse burn wound model. Acta Biomaterialia, 2014. 10(10): p. 4136-4142.
28. Pegalajar-Jurado, A., et al., Nitric oxide-releasing polysaccharide derivative exhibits 8-log reduction against *Escherichia coli, Acinetobacter baumannii* and *Staphylococcus aureus*. Journal of Controlled Release, 2015. 217: p. 228-234.
29. Vogt, C., et al., Fabrication and characterization of a nitric oxide-releasing nanofibrous gelatin matrix. Biomacromolecules, 2013. 14(8): p. 2521-2530.
30. Frost, M. C. and M. E. Meyerhoff, Synthesis, characterization, and controlled nitric oxide release from S-nitrosothiol-derivatized fumed silica polymer filler particles. Journal of Biomedical Materials Research Part A, 2005. 72(4): p. 409-419.
31. Zhang, H., et al., Nitric oxide-releasing fumed silica particles: synthesis, characterization, and biomedical application. Journal of the American Chemical Society, 2003. 125(17): p. 5015-5024.
32. Shin, J. H., S. K. Metzger, and M. H. Schoenfisch, Synthesis of nitric oxide-releasing silica nanoparticles. Journal of the American Chemical Society, 2007. 129(15): p. 4612-4619.
33. Shin, J. H. and M. H. Schoenfisch, Inorganic/organic hybrid silica nanoparticles as a nitric oxide delivery scaffold. Chemistry of Materials, 2007. 20(1): p. 239-249.
34. Soto, R. J., L. Yang, and M. H. Schoenfisch, Functionalized mesoporous silica via an aminosilane surfactant ion exchange reaction: controlled scaffold design and nitric oxide release. ACS applied materials & interfaces, 2016. 8(3): p. 2220-2231.
35. Florke, O. W., et al., Silica, in Ullmann's Encyclopedia of Industrial Chemistry. 2000, Wiley-VCH Verlag GmbH & Co. KGaA.
36. Hetrick, E. M., et al., Anti-biofilm efficacy of nitric oxide-releasing silica nanoparticles. Biomaterials, 2009. 30(14): p. 2782-2789.
37. Hetrick, E. M., et al., Bactericidal efficacy of nitric oxide-releasing silica nanoparticles. Acs Nano, 2008. 2(2): p. 235-246.
38. Antonides1, L. E., Diatomite. USGS Mineral Resources Program, 1997.
39. Calvert, R., Diatomaceous earth. J. Chem. Educ, 1930. 7(12): p. 2829.
40. Gordon, R., et al., The glass menagerie: diatoms for novel applications in nanotechnology. Trends in biotechnology, 2009. 27(2): p. 116-127.
41. Lopez-Alvarez, M., et al., Silicon-hydroxyapatite bioactive coatings (Si-HA) from diatomaceous earth and silica. Study of adhesion and proliferation of osteoblast-like cells. Journal of Materials Science: Materials in Medicine, 2009. 20(5): p. 1131-1136.
42. Basadonna, G., R. J. Huey, and D. Lo, Wound healing with zeolite-based hemostatic devices. 2008, Google Patents.
43. Lahanas, K. M., T. N. Keeler, and D. Toma, Powder compositions. 2000, Google Patents.

44. Moynihan, H. A. and S. M. Roberts, Preparation of some novel S-nitroso compounds as potential slow-release agents of nitric oxide in vivo. J. Chem. Soc., Perkin Trans. 1, 1994(7): p. 797-805.
45. Espeel, P. and F. E. Du Prez, One-pot multi-step reactions based on thiolactone chemistry: a powerful synthetic tool in polymer science. European Polymer Journal, 2015. 62: p. 247-272.
46. Liu, J., et al., Design of 3-(4-carboxybenzoyl)-2-quinolinecarboxaldehyde as a reagent for ultrasensitive determination of primary amines by capillary electrophoresis using laser fluorescence detection. Analytical chemistry, 1991. 63(5): p. 408-412.
47. Ellman, G. L., Tissue sulfhydryl groups. Archives of biochemistry and biophysics, 1959. 82(1): p. 70-77.
48. Pavithra, D. and M. Doble, Biofilm formation, bacterial adhesion and host response on polymeric implants—issues and prevention. Biomedical Materials, 2008. 3(3): p. 034003.
49. Allan, N. D., K. Giare-Patel, and M. E. Olson, An in vivo rabbit model for the evaluation of antimicrobial peripherally inserted central catheter to reduce microbial migration and colonization as compared to an uncoated PICC. BioMed Research International, 2012. 2012.
50. Otto, M., Staphylococcal infections: mechanisms of biofilm maturation and detachment as critical determinants of pathogenicity. Annual review of medicine, 2013. 64: p. 175-188.
51. Kiedrowski, M. R. and A. R. Horswill, New approaches for treating staphylococcal biofilm infections. Annals of the New York Academy of Sciences, 2011. 1241(1): p. 104-121.
52. Waddell, T. G., D. E. Leyden, and M. T. DeBello, The nature of organosilane to silica-surface bonding. Journal of the American Chemical Society, 1981. 103(18): p. 5303-5307.
53. Vandenberg, E. T., et al., Structure of 3-aminopropyl triethoxy silane on silicon oxide. Journal of Colloid and Interface Science, 1991. 147(1): p. 103-118.
54. Zhu, M., M. Z. Lerum, and W. Chen, How to prepare reproducible, homogeneous, and hydrolytically stable aminosilane-derived layers on silica. Langmuir, 2011. 28(1): p. 416-423.
55. Asenath Smith, E. and W. Chen, How to prevent the loss of surface functionality derived from aminosilanes. Langmuir, 2008. 24(21): p. 12405-12409.
56. Feng, X., et al., Functionalized monolayers on ordered mesoporous supports. Science, 1997. 276(5314): p. 923-926.
57. Friedman, A. J., et al., Sustained release nitric oxide releasing nanoparticles: characterization of a novel delivery platform based on nitrite containing hydrogel/glass composites. Nitric Oxide, 2008. 19(1): p. 12-20.
58. Riccio, D. A., J. L. Nugent, and M. H. Schoenfisch, Stober synthesis of nitric oxide-releasing S-nitrosothiol-modified silica particles. Chemistry of Materials, 2011. 23(7): p. 1727-1735.
59. Stöber, W., A. Fink, and E. Bohn, Controlled growth of monodisperse silica spheres in the micron size range. Journal of colloid and interface science, 1968. 26(1): p. 62-69.
60. Aw, M. S., et al., Porous silica microshells from diatoms as biocarrier for drug delivery applications. Powder technology, 2012. 223: p. 52-58.
61. Jaganathan, H. and B. Godin, Biocompatibility assessment of Si-based nano- and microparticles. Advanced drug delivery reviews, 2012. 64(15): p. 1800-1819.
62. Anglin, E. J., et al., Porous silicon in drug delivery devices and materials. Advanced drug delivery reviews, 2008. 60(11): p. 1266-1277.
63. Stewart, P. S. and J. W. Costerton, Antibiotic resistance of bacteria in biofilms. The lancet, 2001. 358(9276): p. 135-138.
64. Costerton, J. and P. Stewart, Biofilms and device-related infections. Persistent bacterial infections, 2000: p. 423-437.
65. Davies, J., Inactivation of antibiotics and the dissemination of resistance genes. Science, 1994. 264(5157): p. 375-383.
66. Fang, F. C., Perspectives series: host/pathogen interactions. Mechanisms of nitric oxide-related antimicrobial activity. Journal of Clinical Investigation, 1997. 99(12): p. 2818.
67. Feelisch, M., The use of nitric oxide donors in pharmacological studies. Naunyn-Schmiedeberg's archives of pharmacology, 1998. 358(1): p. 113-122.
68. Hetrick, E. M. and M. H. Schoenfisch, Antibacterial nitric oxide-releasing xerogels: Cell viability and parallel plate flow cell adhesion studies. Biomaterials, 2007. 28(11): p. 1948-1956.
69. Sundaram, J., et al., Antimicrobial and Physicochemical Characterization of Biodegradable, Nitric Oxide-Releasing Nanocellulose-Chitosan Packaging Membranes. Journal of agricultural and food chemistry, 2016.
70. Charville, G. W., et al., Reduced bacterial adhesion to fibrinogen-coated substrates via nitric oxide release. Biomaterials, 2008. 29(30): p. 4039-4044.
71. Mihu, M. R., et al., The use of nitric oxide releasing nanoparticles as a treatment against *Acinetobacter baumannii* in wound infections. Virulence, 2010. 1(2): p. 62-67.
72. Engelsman, A. F., et al., Antimicrobial effects of an NO-releasing poly (ethylene vinylacetate) coating on soft-tissue implants in vitro and in a murine model. Acta biomaterialia, 2009. 5(6): p. 1905-1910.
73. Lee, Y.-H., et al., Cytotoxicity, oxidative stress, apoptosis and the autophagic effects of silver nanoparticles in mouse embryonic fibroblasts. Biomaterials, 2014. 35(16): p. 4706-4715.
74. Park, E.-J., et al., Silver nanoparticles induce cytotoxicity by a Trojan-horse type mechanism. Toxicology in Vitro, 2010. 24(3): p. 872-878.
75. Baldi, C., et al., Effects of silver in isolated rat hepatocytes. Toxicology letters, 1988. 41(3): p. 261-268.
76. AshaRani, P., et al., Cytotoxicity and genotoxicity of silver nanoparticles in human cells. ACS nano, 2008. 3(2): p. 279-290.
77. Cheng, X., et al., Revealing silver cytotoxicity using Au nanorods/Ag shell nanostructures: disrupting cell membrane and causing apoptosis through oxidative damage. RSC Advances, 2013. 3(7): p. 2296-2305.
78. Wachter, H., et al., Diatomaceous earth lowers blood cholesterol concentrations. European journal of medical research, 1998. 3(4): p. 211-215.
79. West, N., J. Hughes, and M. Addy, Dentine hypersensitivity: the effects of brushing toothpaste on etched and unetched dentine in vitro. Journal of oral rehabilitation, 2002. 29(2): p. 167-174.
80. Yu, T., A. Malugin, and H. Ghandehari, The impact of silica nanoparticle design on cellular toxicity and hemolytic activity. ACS nano, 2011. 5(7): p. 5717.
81. Tarn, D., et al., Mesoporous silica nanoparticle nanocarriers-biofunctionality and biocompatibility. Accounts of chemical research, 2013. 46(3): p. 792.

82. Zhang, H., et al., Processing pathway dependence of amorphous silica nanoparticle toxicity-colloidal versus pyrolytic. Journal of the American Chemical Society, 2012. 134(38): p. 15790.

We claim:

1. A nitric oxide-releasing material comprising:
a mesoporous diatomaceous earth core having an outer surface with an aminosilane covalently bonded to the outer surface, wherein the aminosilane is covalently bonded to the outer surface of the mesoporous diatomaceous earth core by a silicon atom of the aminosilane; and
a S-nitroso-N-acetyl-penicillamine group covalently bonded to the amino group of the aminosilane,
wherein the S-nitroso-N-acetyl-penicillamine group covalently bonded to the amino group of the aminosilane has the following formula

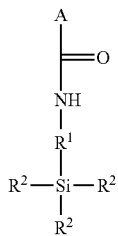

where A is the S-nitroso-N-acetyl-penicillamine group;
where $R^1$ is a substituted or unsubstituted $C_1$-$C_{20}$ alkyl, a substituted or unsubstituted $C_1$-$C_{20}$ heteroalkyl, a substituted or unsubstituted $C_2$-$C_{20}$ alkenyl, a substituted or unsubstituted $C_2$-$C_{20}$ herteroalkenyl, a substituted or unsubstituted $C_1$-$C_{20}$ alkoxy, or a substituted or unsubstituted $C_1$-$C_{20}$ heteroalkoxy;
where each occurrence of $R^2$ is independently a substituted or unsubstituted $C_1$-$C_{20}$ alkyl, a substituted or unsubstituted $C_1$-$C_{20}$ heteroalkyl, a substituted or unsubstituted $C_2$-$C_{20}$ alkenyl, a substituted or unsubstituted $C_2$-$C_{20}$ herteroalkenyl, a substituted or unsubstituted $C_1$-$C_{20}$ alkoxy, a substituted or unsubstituted $C_1$-$C_{20}$ heteroalkoxy, or a bond to an oxygen atom on the outer surface of the mesoporous diatomaceous earth core wherein at least one occurrence of $R^2$ is a bond to an oxygen atom on the outer surface of the mesoporous diatomaceous earth core.

2. The nitric oxide-releasing material according to claim 1, wherein the nitric oxide-releasing material has a nitric oxide content of about 0.025 µmol to about 0.05 µmol per mg of the nitric oxide-releasing material.

3. The nitric oxide-releasing material according to claim 1, wherein the nitric oxide-releasing material has a half-life for nitric oxide release of about 20 hours to about 40 hours.

4. The nitric oxide-releasing material according to claim 1, wherein the nitric oxide-releasing material has an average pore size of about 300 nm to about 600 nm.

5. The nitric oxide-releasing material according to claim 1, wherein the nitric oxide-releasing material is a particle having a longest dimension of about 10 µm to about 20 µm.

6. The nitric oxide-releasing material according claim 1, wherein $R^1$ is a substituted or unsubstituted $C_1$-$C_{12}$ alkyl.

7. The nitric oxide-releasing material according claim 1, wherein the aminosilane is 3-aminopropyl)triethoxysilane (APTES), N-(6-aminohexyl)aminomethyltriethoxysilane (AHAMTES), or 3-aminopropyldimethylethoxysilane (APDMES).

8. The nitric oxide-releasing material according claim 1, wherein the aminosilane is 3-aminopropyl)triethoxysilane (APTES).

9. A medical device having at least one surface, wherein the surface comprises the nitric oxide-releasing material having a structure according to claim 1.

10. The medical device according to claim 9, wherein the medical device is a urinary catheter, a vascular catheter, a graft, a stent, or a hydrogel strip.

* * * * *

UNITED STATES PATENT AND TRADEMARK OFFICE
CERTIFICATE OF CORRECTION

| | | |
|---|---|---|
| PATENT NO. | : 11,117,808 B2 | Page 1 of 1 |
| APPLICATION NO. | : 16/051812 | |
| DATED | : September 14, 2021 | |
| INVENTOR(S) | : Hitesh Handa et al. | |

It is certified that error appears in the above-identified patent and that said Letters Patent is hereby corrected as shown below:

In the Specification

At Column 1, Lines 18-21, under the Statement Regarding Federally Sponsored Research or Development should read as follows:
This invention was made with government support under 200-2016-91933 awarded by the Centers for Disease Control and Prevention, and R01 HL134899, and HL111213 awarded by the National Institutes of Health. The government has certain rights in the invention.

Signed and Sealed this
Twelfth Day of November, 2024

Katherine Kelly Vidal
*Director of the United States Patent and Trademark Office*